US006492185B1

(12) United States Patent
Kundu

(10) Patent No.: US 6,492,185 B1
(45) Date of Patent: *Dec. 10, 2002

(54) IMMUNOASSAY FOR DETECTION OF VERY LOW DENSITY LIPOPROTEIN AND ANTIBODIES USEFUL THEREFOR

(75) Inventor: Samar K. Kundu, Libertyville, IL (US)

(73) Assignee: Abbott Laboratories, Abbott Park, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/008,059

(22) Filed: Jan. 16, 1998

(51) Int. Cl.$^7$ ............................................... G01N 33/53
(52) U.S. Cl. ..................... 436/518; 435/7.1; 435/7.9; 435/7.92; 435/7.93; 435/7.94; 436/514; 436/547; 436/548; 436/13; 530/380; 530/388.1
(58) Field of Search ..................... 435/7.1, 7.9, 7.92, 435/7.93, 7.904; 436/518, 547, 548, 13; 530/380, 388.1

(56) References Cited

PUBLICATIONS

J.D. Belcher, et al., "Measurement of Low Density Lipoprotein Cholesterol Concentration", ed. N. Rifai and G.R. Warnick, *Methods For Clinical Laboratory Measurement of Lipid and Lipoprotein Risk Factors*, AACC Press (1991), pp. 75–86.

D.J. Betteridge, "Lipids, Diabetes, and Vascular Disease: The Time to Act", *Diabetic Medicine*, vol. 6 (1989), pp. 195–218.

D.M. DeLong, et al., "A Comparison of Methods for the Estimation of Plasma Low–and Very Low–Density Lipoprotein Cholesterol", *JAMA*, vol. 256 (1986), pp. 2372–2377.

W.T. Friedewald et al., "Estimation of the Concentration of Low–Density Lipoprotein Cholesterol in Plasma, Without Use of the Preparative Ultracentrifuge", *Clinical Chemistry*, vol. 18 (1972), pp. 499–502.

S.H. Gianturco, et al., "Triglyceride–rich lipoproteins and their role in atherogenesis", *Current Opinion in Lipidology*, vol. 2 (1991), pp. 324–328.

S.M. Grundy, et al., "Two Different Views of the Relationship of Hypertriglyceridemia to Coronary Heart Disease", *Arch Intern Med*, vol. 152 (1992), pp. 28–34.

E. Hurt–Camejo, et al., "Cellular Consequences of the Association of ApoB Lipoproteins With Proteglycans" *Arteriosclerosis, Thrombosis, and Vascular Biology*, vol. 17 (1997), pp. 1011–1017.

M.L. Larsen et al., "Triglyceride–lowering agents: fibrates and nicotinic acid", *Current Opinion in Lipidology*, vol. 4 (1993), pp. 34–40.

V. Manninen, et al., "Joint Effects of Serum Triglyceride and LDL Cholesterol and HDL Cholesterol Concentrations on Coronary Heart Disease Risk in the Helsinki Heart Study", *Circulation*, vol. 85 (1992), pp. 37–45.

J.R. McNamara, et al., "Calculated Values for Low–Density Lipoprotein Cholesterol in the Assessment of Lipid Abnormalities and Coronary Disease Risk", *Clin. Chem.*, vol. 36 (1990), pp. 36–42.

E.J. Schaefer, et al., "Familial lipoprotein disorders and premature coronary artery disease", *Current Opinion in Lipodology*, vol. 4 (1993), pp. 288–298.

E.J. Schaefer, et al., "Pathogenesis and Management of Lipoprotein Disorders", *The New England Journal of Medicine*, vol. 312 (1985), pp. 1300–1310.

E.A. Stein, et al, "National Cholesterol Education Program Recommendations for Triglyceride Measurement: Executive Summary", *Clin. Chem.*, vol. 41 (1995), pp. 1421–1426.

G.R. Warnick, et al., "Estimating Low–Density Lipoprotein Cholesterol by the Friedewald Equation Is Adequate for Classifying Patients on the Basis of Nationally Recommended Cutpoints", *Clin. Chem.*, vol. 36 (1990), pp. 15–19.

Young et al., Clin. Chem., 32(8):1484–1490, 1986.*

Cambell, A., Monoclonal Antibody Technology. pp. 186–215, 1986.*

* cited by examiner

Primary Examiner—Bao-Thuy L. Nguyen
(74) Attorney, Agent, or Firm—Dianne Casuto

(57) ABSTRACT

The present invention provides a method for directly measuring apolipoprotein B-100 (apoB) or cholesterol associated with very low density lipoprotein (VLDL) in a fluid sample. In one embodiment the method involves the specific capture of intact VLDL particles from a fluid sample with a specific VLDL binding agent. The quantity of VLDL-apoB present in the sample is then measured by detecting the amount of VLDL-apoB bound to the binding agent-VLDL complexes formed in the reaction. In an alternative embodiment of the method, intact VLDL particles from a fluid sample are also captured with a specific VLDL binding agent and thereafter the cholesterol associated with the bound VLDL is determined. The cholesterol contained in the binding-agent-VLDL complexes can be detected by reacting the complexes with labeled cholesterol specific binding agents and measuring the amount of label bound therto, or by releasing the cholesterol in the complexes and measuring the amount of cholesterol released. VLDL specific binding reagents are also provided.

12 Claims, 11 Drawing Sheets

IMMUNOASSAY FOR DETECTION OF VERY LOW DENSITY LIPOPROTEIN AND ANTIBODIES USEFUL THEREFOR

FIELD OF THE INVENTION

The present invention relates to diagnostic methods for detection and quantification of lipoproteins and cholesterol associated with lipoproteins. More particularly, the invention relates to assay methods for direct measurement of apolipoprotein B (apoB) associated very low density lipoproteins (VLDL) and cholesterol associated with VLDL using specific monoclonal antibodies.

BACKGROUND OF THE INVENTION

Very low density lipoprotein (VLDL) constitutes one of the major plasma lipoproteins. VLDL particles are synthesized in the liver and are involved in triglyceride metabolism and transport of these lipids from the liver. The end products of VLDL catabolism are low density lipoproteins (LDL), another major class of lipoprotein particles in plasma.

It has been suggested that disturbances in the metabolism of apoB containing lipoproteins such as VLDL and LDL correlate with incidences of atherosclerosis (Hurt-Camejo et al. (1997) Arteriosclerosis, Thrombosis, and Vascular Biology 17(6): 1011–1017). Furthermore, an increase in VLDL levels has been associated with hypertriglycerimedia, hyperlipidemia or familial combined hyperlipidemia (Betteridge (1989) Diabet Med 6: 195–218; Schaefer et al. (1985) New Engl J. Med 312: 1300–1310; Shaefer et al. (1993) Curr Opin Lipidol 4: 288–298). Hyperglyceridemia also has been shown to correlate with an increased incidence of coronary heart disease (Gianturco et al. (1991) Curr Opin Lipidol 2: 324–328; Manninen et al. (1992) Circulation 85: 37–45; Grundy et al. (1992) Arch Intern Med 152: 28–34). Many patients with hyperglycerimedia have very low levels of high density lipoprotein (HDL), another major lipoprotein in plasma. It is recommended to treat patients with coronary heart disease who concurrently have hypertriglyceridemia and low levels of HDL with drugs and pharmacologic reagents, even when these patients have acceptable levels of total and LDL cholesterol (Larsen et al. (1993) Curr Opin Lipidol 4: 34–40); Stein and Myers (1995) Clin Chem 41: 1421–1426).

Two methods are presently used for the quantitation of VLDL, both of which involve the measurement of VLDL-cholesterol. The first method uses the factor triglyceride/5 as VLDL-cholesterol concentration (Friedewald et al. (1972) Clin Chem 18: 499–502). In this method, it is assumed that all plasma triglycerides are associated with VLDL and chylomicrons and that other VLDL remnants are not present. Chylomicrons are microscopic lipid particles that appear in the blood transiently after a fat-containing meal, are rich in triglycerides and usually have no significant effect on the total-cholesterol concentration. Although these assumptions are not strictly true, the factor triglyceride/5 usually provides good measure of VLDL-cholesterol when the subject is fasting and the triglyceride concentrations do not exceed 400 mg/dL.

The second method for quantitating VLDL uses ultracentrifugation. In this method, an aliquot of plasma is used to measure the total cholesterol concentration in the sample. A second aliquot of plasma is centrifuged (105,000× g) at a plasma density concentration of 1.006 g/mL for 18 hours at 4° C. After centrifugation, the upper layer containing VLDL is quantitatively removed and the cholesterol concentration in the isolated VLDL is measured. Alternatively, an aliquot of the remaining bottom layer, which does not contain VLDL, is used to measure the cholesterol concentration ([d >1.006 g/mL chol]). The cholesterol concentration of VLDL ([VLDL-chol]) is then calculated using the following equation:

$$[VLDL\text{-chol}]=[\text{Total-chol}]-[d>1.006 \text{ g/mL chol}]$$

Both methodologies suffer from a variety of problems. For example, the use of the factor triglyceride/5 is unacceptable in cases where a subject is not fasting, or where triglyceride concentrations exceed 400 mg/dL. Moreover, this method should not be used for Type III hyperlipoproteinemic patients that contain floating beta-VLDL (Belcher et al. (1991) Methods for Clinical Laboratory Measurement of Lipid and Lipoprotein Risk Factors, Eds. Rifai and Warnick, MCC Press, Washington, D.C., pp. 75–86). Although several studies have been conducted to determine better ways to measure VLDL-cholesterol concentrations (McNamara et al. (1990) Clin Chem 36: 36–42; Warnick et al. (1990) Clin Chem36: 15–19; Delong et al. (1986) JAMA 256: 2372–2377), no significant improvement has yet been made.

The problem with the ultracentrifugation method of VLDL-cholesterol quantitation is that it is both time consuming and expensive to perform. Furthermore, since the method requires specialized equipment, facilities and laboratory skills, it is not suitable for routine analysis of patient samples. To complicate these matters, no alternative methodologies for measuring VLDL, such as assays which measure apoB associated with VLDL, are currently available, either for analysis of patient samples or for research purposes. Thus, there is a need for rapid, easily performed, accurate and cost effective methods for quantitating VLDL.

SUMMARY OF THE INVENTION

An objective of this invention is to generate monoclonal antibodies that are specific for VLDL. Another object of this invention is to develop a method of directly measuring apolipoprotein B-100 (apoB) and cholesterol associated with VLDL from plasma easily, cheaply, quickly and accurately without the need of highly trained technicians or expensive equipment such as ultracentrifuges. Yet another object of this invention is to directly measure VLDL-cholesterol without the analytical variability generally associated with the present method of quantitative removal of VLDL layer in the ultracentrifugation method even with highly trained technicians.

In one embodiment, the present invention provides a method for determining the amount of apoB associated with VLDL in a sample comprising the steps of: (a) mixing a sample and a VLDL-specific binding agent for a time and under conditions to form binding-agent-VLDL complexes; and (b) determining the amount of apoB associated with VLDL bound to the binding-agent-VLDL complexes. In a preferred embodiment, the VLDL-specific binding agent is coupled to a solid support. In a more preferred embodiment, the solid support is separated from the sample before determining the amount of apoB bound to the binding-agent-VLDL complexes. Preferred solid supports include nitrocellulose, latex, nylon, polystyrene beads, particles, magnetic particles, and glass fiber. In these embodiments, the VLDL-specific binding agent is an antibody or fragment thereof that binds to substantially all VLDL, to LDL at less than about 10% of VLDL binding, to IDL at less than about 10% of VLDL binding, and to HDL at less than about 10% of VLDL binding. Preferably, the antibody is a monoclonal antibody. More preferably, the monoclonal antibody is selected from the group consisting of 18-571-312, 18-140-196, 18-459-172, and 18-358-211. A most preferred monoclonal antibody is 18-358-211.

In yet another embodiment, the method further comprises the step of separating the binding-agent-VLDL complexes prior to determining the amount of apoB associated with VLDL. In a preferred method of this embodiment, the VLDL-specific binding agent is conjugated to a first charged substance and the separation step comprises contacting the binding-agent-VLDL complexes with an insoluble solid phase material which is oppositely charged with respect to the first charged substance, such that the solid phase material attracts and attaches to the first charged substance and separating the solid phase material and the sample. Preferably, the charged substances are anionic and cationic monomers or polymers.

In another embodiment, the invention provides a method for determining the amount of apoB associated with VLDL in a sample comprising the steps of: contacting the sample with an indicator reagent wherein the indicator reagent is a monoclonal antibody or fragment thereof that specifically binds to apoB associated with VLDL and with a solid support coated with VLDL for a time and under conditions to permit binding of the indicator reagent with the VLDL in the sample and with the bound VLDL and determining the amount of apoB associated with VLDL in the test sample by detecting the reduction in binding of the indicator reagent to the solid support as compared to the signal generated from a negative sample to indicate the presence of VLDL in the test sample. In this embodiment, the indicator reagent is preferably the monoclonal antibody 18-358-211.

In another embodiment, the invention provides a method for determining the amount of cholesterol associated with VLDL in a sample and comprises the steps of mixing a sample and a VLDL-specific binding agent for a time and under conditions to form binding-agent-VLDL complexes; and determining the amount of cholesterol bound to the binding-agent-VLDL complexes. In a preferred embodiment, the VLDL-specific binding agent is coupled to a solid support. In a more preferred embodiment, the solid support is separated from the sample before determining the amount of cholesterol bound to the binding-agent-VLDL complexes. Preferred solid supports include nitrocellulose, latex, nylon, polystyrene, beads, particles, magnetic particles, and glass fiber. In these embodiments, the VLDL-specific binding agent is an antibody or fragment thereof that binds to substantially all VLDL, to LDL at less than about 10% of VLDL binding, to IDL at less than about 10% of VLDL binding, and to HDL at less than about 10% of VLDL binding. Preferably, the antibody is a monoclonal antibody. More preferably, the monoclonal antibody is selected from the group consisting of 18-571-312, 18-140-196, 18-459-172, and 18-358-211.

In one alternative embodiment, determining the amount of cholesterol comprises releasing the cholesterol bound to the binding agent-VLDL complexes and measuring the amount of cholesterol released. In a second alternative embodiment, determining the amount of cholesterol comprises mixing the binding-agent-VLDL complexes with a cholesterol specific binding agent coupled to a detectable label for a time and under conditions suitable to form binding-agent-VLDL-cholesterol specific binding agent complexes and determining the amount of label bound to the binding-agent-VLDL-cholesterol specific binding agent complex.

In yet another embodiment, the method further comprises the step of separating the binding-agent-VLDL complexes prior to determining the amount of cholesterol associated with VLDL. In a preferred embodiment, the VLDL-specific binding agent is conjugated to a first charged substance and the separation step comprises contacting the binding-agent-VLDL complexes with an insoluble solid phase material which is oppositely charged with respect to the first charged substance, such that the solid phase material attracts and attaches to the first charged substance and separating the solid phase material and the sample. Preferably, the charged substances are anionic and cationic monomers or polymers. One alternative embodiment of this method involves releasing the cholesterol bound to the binding-agent-VLDL complexes and measuring the amount of cholesterol released. A second alternative embodiment involves mixing the binding-agent-VLDL complexes with a cholesterol specific binding agent coupled to a detectable label such that a second complex is formed and determining the amount of label bound to the second complex.

The present invention also provides an antibody or fragment thereof specific for VLDL wherein the antibody binds to substantially all VLDL, to LDL at less than about 10% of VLDL binding, to IDL at less than about 10% of VLDL binding, and to HDL at less than about 10% of VLDL binding. Preferably, the antibody is selected from the group consisting of 18-571-312, 18-140-196, 18-459-172, and 18-358-211. A most preferred antibody is produced by a hybridoma cell line having ATCC Accession No. HB-12392.

The present invention also provides a hybridoma cell line that produces a monoclonal antibody which binds to substantially all VLDL, to LDL at less than about 10% of VLDL binding, to IDL at less than about 10% of VLDL binding, and to HDL at less than about 10% of VLDL binding. Preferably, the hybridoma cell line produces a monoclonal antibody selected from the group consisting of 18-571-312, 18-140-196, 18-459-172, and 18-358-211. A most preferred hybridoma cell has ATCC Accession No. HB-12392.

The present invention yet further provides a monoclonal antibody specific for VLDL prepared by the method comprising the steps of: (a) immunizing a mouse or a rat with Apo CIII; (b) making a suspension of the mouse or rat spleen cells; (c) fusing the spleen cells with mouse or rat myeloma cells in the presence of a fusion promoter; (d) culturing the fused cells; (e) determining the presence of anti-VLDL antibody in the culture media; (f) cloning a hybridoma producing antibody that binds to substantially all VLDL, to LDL at less than about 10% of VLDL binding, to IDL at less than about 10% of VLDL binding, and to HDL at less than about 10% of LDL binding; and (g) obtaining the antibody from the hybridoma.

DETAILED DESCRIPTION OF THE INVENTION

I. Definitions

Figure 1:
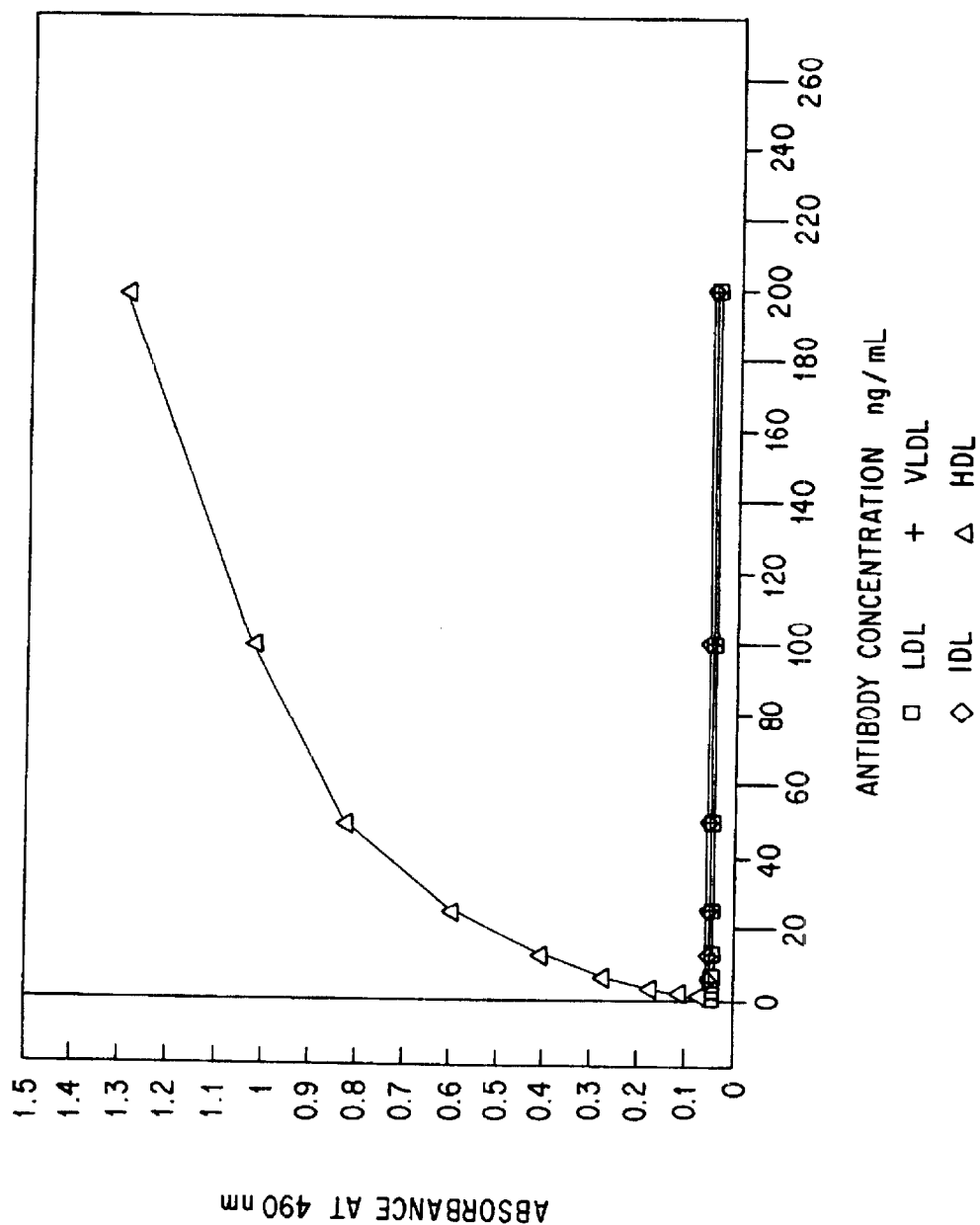
FIG. 1: Typical antibody titer plots of the monoclonal antibody 18-358-211 obtained by incubating microtiter plates with LDL, VLDL, HDL, and IDL bound to the plates in separate wells and measuring the antibody bound to the lipoproteins by an ELISA.

Unless otherwise stated, the following terms shall have the following meanings:

The term "fluid sample" or "test sample", as used herein, includes biological samples which can be tested by the methods of the present invention and include human and animal body fluids such as whole blood, serum, plasma, cerebrospinal fluid, urine, lymph fluids, and various external secretions of the respiratory, intestinal and genitourinary tracts, tears, saliva, milk, white blood cells, and the like, and biological fluids such as cell culture supernatants. Any substance which can be adapted for testing with the reagents described herein and assay formats of the present invention are contemplated to be within the scope of the present invention.

The term "analyte", as used herein, is the substance to be detected which may be present in the test sample. The analyte can be any substance for which there exists a naturally occurring specific binding member (such as, an antibody), or for which a specific binding member can be prepared. Thus, an analyte is a substance that can bind to one or more specific binding members. Analytes include but are not limited to antigenic substances, haptens, antibodies, and combinations thereof. The term "anti-analyte", as used herein, refers to an analyte specific binding member.

A "specific binding member" or "specific binding agent", as used herein, refers to one member or partner of a specific binding pair. A "specific binding pair" refers to two different molecules wherein one of the molecules through chemical or physical means specifically binds to the second molecule. A typical example of specific binding members or agents which constitute a specific binding pair are an antigen and an antibody. Other specific binding pairs can include biotin and avidin, carbohydrates and lectins, cofactors and enzymes, enzyme inhibitors and enzymes, effector and receptor molecules, and the like. Furthermore, specific binding pairs can include members that are analogs of the original specific binding members, for example, an analyte-analog. Immunoreactive specific binding members include antigens, antigen fragments, antibodies, antibody fragments, both monoclonal and polyclonal, and complexes thereof.

The term "ancillary specific binding member", as used herein, refers to a specific binding member which binds to an analyte specific binding member and includes for example, an antibody to an antibody.

The term "hapten" as used herein, refers to a partial antigen or non-protein binding member which is capable of binding to an antibody, but which is not capable of eliciting antibody formation unless coupled to a carrier protein.

A "capture reagent" as used herein, refers to an unlabeled specific binding member which is specific either for the analyte as in a sandwich assay, for the indicator reagent or analyte as in a competitive assay, or for an ancillary specific binding member, as in an indirect assay. The capture reagent can be directly or indirectly bound to a solid phase material before the performance of the assay or during the performance of the assay, thereby enabling the separation of immobilized complexes from the test sample.

An "indicator reagent" as used herein comprises a specific binding member conjugated to a label. Indicator reagents include labeled specific binding members which directly bind to analytes of interest and labeled ancillary specific binding members.

"Solid phases" ("solid supports") are known to those in the art and include the walls of wells of a reaction tray, test tubes, polystyrene beads, magnetic beads, nitrocellulose strips, membranes, microparticles such as latex particles, sheep (or other animal) red blood cells, and Duracytes® (red blood cells "fixed" by pyruvic aldehyde and formaldehyde, available from Abbott Laboratories, Abbott Park, Ill.) and others. The "solid phase" is not critical and can be selected by one skilled in the art. Thus, latex particles, microparticles, magnetic or non-magnetic beads, membranes, plastic tubes, walls of microtiter wells, glass or silicon chips, sheep (or other suitable animal's) red blood cells and Duracytes® are all suitable examples. Suitable methods for immobilizing peptides on solid phases include ionic, hydrophobic, covalent interactions and the like. A "solid phase", as used herein, refers to any material which is insoluble, or can be made insoluble by a subsequent reaction. The solid phase can be chosen for its intrinsic ability to attract and immobilize the capture reagent. Alternatively, the solid phase can retain an additional receptor which has the ability to attract and immobilize the capture reagent. The additional receptor can include a charged substance that is oppositely charged with respect to the capture reagent itself or to a charged substance conjugated to the capture reagent. As yet another alternative, the receptor molecule can be any specific binding member which is immobilized upon (attached to) the solid phase and which has the ability to immobilize the capture reagent through a specific binding reaction. The receptor molecule enables the indirect binding of the capture reagent to a solid phase material before the performance of the assay or during the performance of the assay. The solid phase thus can be a plastic, derivatized plastic, magnetic or non-magnetic metal, glass or silicon surface of a test tube, microtiter well, sheet, bead, microparticle, chip, sheep (or other suitable animal's) red blood cells, Duracytes® and other configurations known to those of ordinary skill in the art.

It is contemplated and within the scope of the present invention that the solid phase also can comprise any suitable porous material with sufficient porosity to allow access by detection antibodies and a suitable surface affinity to bind antigens. Microporous structure generally are preferred, but materials with gel structure in the hydrated state may be used as well. Such useful solid supports include but are not limited to nitrocellulose and nylon. It is contemplated that such porous solid supports described herein preferably are in the form of sheets of thickness from about 0.01 to 0.5 mm, preferably about 0.1 mm. The pore size may vary within wide limits, and preferably is from about 0.025 to 15 microns, especially from about 0.15 to 15 microns. The surface of such supports may be activated by chemical processes which cause covalent linkage of the antigen or antibody to the support. The irreversible binding of the antigen or antibody is obtained, however, in general, by adsorption on the porous material by poorly understood hydrophobic forces. Other suitable solid supports are known in the art.

The term "label", as used herein, refers to any substance which can be attached to specific binding agents, such as antibodies, antigens, cholesterol binding agents, Lp(a) specific binding agents and analogs thereof, and which is capable of producing a signal that is detectable by visual or instrumental means. Various suitable labels for use in the present invention can include chromogens, catalysts, fluorescent compounds, chemiluminescent compounds, radioactive elements, colloidal metallic (such as gold), non-metallic (such as selenium) and dye particles (such as the particles disclosed in U.S. Pat. Nos. 4,313,734, 4,954,452, and 4,373,932), enzymes, enzyme substrates, and organic polymer latex particles (as disclosed in co-owned U.S. Pat. No. 5,252,459, issued Oct. 12, 1993), liposomes or other vesicles containing such signal producing substances, and the like. A large number of enzymes suitable for use as labels are disclosed in U.S. Pat. No. 4,275,149. Such enzymes include phosphatases and peroxidases, such as alkaline phosphatase and horseradish peroxidase which are used in conjunction with enzyme substrates, such as nitro blue tetrazolium, 3,5',5,5'-tetranitrobenzidine, 4-methoxy-1-naphthol, 4-chloro-1-naphthol, 5-bromo-4-chloro-3-indolyl phosphate, chemiluminescent enzyme substrates such as the dioxetanes described in U.S. Pat. Nos. 4,857,652 (issued Aug. 15, 1989), U.S. Pat. No. 4,931,223 (issued Jun. 5, 1990), U.S. Pat. No. 4,931,569 (issued Jun. 5, 1990), U.S. Pat. No. 4,962,192 (issued Oct. 9, 1990), and U.S. Pat. No. 4,978,614 (issued December 18, 1990), and derivatives and analogs thereof. Fluorescent compounds such as fluorescein, phycobiliprotein, rhodamine and the like, including their derivatives and analogs are suitable for use as labels.

The linking of labels, i.e. labeling of peptides and proteins is well known to those of ordinary skill in the art. For example, monoclonal antibodies produced by a hybridoma can be labeled by metabolic incorporation of radioisotope-containing amino acids provided as a component in the culture medium. (See, for example, Galfre et al., (1981) Meth. Enzymol., 73: 3–46). The techniques of protein conjugation or coupling through activated functional groups are particularly applicable. (See, Avrameas et al., (1978) Scand. J. Immunol., 8(7): 7–23. Rodwell et al. (1984) Biotech., 3: 889–894 and U.S. Pat. No. 4,493,795).

Cholesterol binding agents bind specifically to cholesterol and include digitonin, tomatine, filipin, amphotericin B and specific binding proteins such as polyclonal and monoclonal antibodies and other synthetic and recombinant proteins that specifically bind cholesterol, cholesterol esters and/or the cholesterol associated with lipoprotein particles. A number of cholesterol binding agents are known in the literature. These include saponins such as digitonin (Berezin et al. (1980) Vopr Med Khim 26: 843–846; Tsybul's kaya et al. (1986) Bioorg Khim 12: 1391–1395), tomatine (Schultz and Sanders (1957) Z Physiol Chem. 308: 122–126; Eskelson et al. (1967) Clin Chem 13: 468–474), filipin (Boernig et al. (1974) Acta Histochem 50: 110–115; Behoke et al. (1984) Eur J Cell Biol 35: 200–205), amphotericin B (Braitburg et al. (1984) J. Infect Dis 149: 986–997), Triterpene Glycoside Halotoxin Al and related compounds (Ivanov et al. (1986) Vopr Med Khim 32: 132–134). Both monoclonal and polyclonal antibodies to cholesterol are also known (J Immunol (1964) 92: 515; Nature (1965) 407: Proc Natl Acad Sci USA (1988) 85: 1902).

Digitonin, tomatine, amphotericin B and anti-cholesterol antibodies can be used in the quantitation of cholesterol and its esters in lipoprotein particles. Digitonin and tomatine can be chemically modified and then conjugated to horseradish peroxidase (HRPO) and alkaline phosphatase (AP). Amphotericin B and anti-cholesterol antibodies can be coupled directly to HRPO and AP. These four HRPO and AP conjugates bind to cholesterol and its esters associated with VLDL. The binding affinity of the enzyme conjugates to VLDL follows the order: digitonin>tomatine>anti-cholesterol antibodies >amphotericin B. Because digitonin conjugates and tomatine conjugates bound more effectively to the cholesterol components of VLDL, these conjugates are preferred in the present invention.

II. The Invention

The present invention provides a method(s) for determining the amount of apoB associated with VLDL in a fluid sample. A VLDL-specific binding agent and a sample are mixed and incubated for a time and under conditions suitable to form binding agent-VLDL complexes. Thereafter, the amount of apoB associated with the VLDL present in the sample is determined from the amount of VLDL present in the binding-agent-VLDL complexes. The present invention also provides methods for determining the amount of cholesterol associated with VLDL in a fluid sample. In this case, a VLDL-specific binding agent and a sample are mixed and incubated as described above; thereafter the amount of cholesterol associated with the VLDL in the complex is measured. The present invention also provides reagents, such as, for example, VLDL-specific binding agents, for use in the methods described herein.

a. Reagents

VLDL-specific binding agents of the present invention include VLDL-specific binding proteins, such as monoclonal (Mab) and polyclonal antibodies (Pab) and other VLDL specific synthetic or recombinant proteins that specifically bind VLDL particles. Preferably, the VLDL-specific binding agent is selective for only VLDL, but some recognition of or binding to other lipoproteins can be tolerated. For example, an antibody selected for its ability to bind only to VLDL particles present in a sample can minimally capture other lipoproteins (i.e bind other lipoproteins by up to 10% of VLDL binding and still be utilized in the invention. In addition, preferably the VLDL-specific monoclonal antibody should not cross-react with non-lipoprotein materials present in a sample. In a more preferred embodiment, a VLDL-specific binding agent selectively binds to VLDL, but not to other lipoproteins. For example, a more preferred VLDL specific binding agent binds only to VLDL and not to other lipoproteins, such as HDL, LDL, IDL, and Lp(a). A most preferred VLDL specific binding agent is a monoclonal antibody.

The term antibody is also meant to include both intact molecules as well as fragments thereof, such as, for example, Fab and F(ab')$^2$ which are capable of binding antigen. Fab and F(ab')$^2$ fragments lack the Fc fragment of intact antibody and may have less non-specific binding than an intact antibody (Wahl, et ai., J. Nucl Med. 24: 316–325, 1983). Such fragments also may be used for the detection and quantitation of VLDL cholesterol particles according to the methods disclosed herein in the same manner as intact antibodies. Such fragments are well known in the art and are typically produced by enzymatic degradation of an antibody, such as with pepsin, papain, or trypsin. Alternatively, antibodies and antibody fragments can be prepared using recombinant antibody methods such as those described in U.S. patent applications Ser. Nos. 513,957, 693,249, 789,619, 776,391, 799,770, 799,772, and 809,083, wherein antibodies or antibody fragments are produced from the RNA of an antibody producing B-cell from an immunized animal, such as a rat or mouse, using known recombinant techniques.

VLDL-specific binding agents according to the present invention also include bacteriophage described in U.S. Pat. No. 4,797,363. Bacteriophage tail or head segments are capable of selectively binding antigens. By mutation and selection processes, bacteriophage having the necessary binding characteristics to selectively bind lipoprotein cholesterol particles can be obtained.

VLDL-specific binding agents according to the present invention also include nucleic acid sequences, such as DNA and RNA, which selectively bind to lipoprotein cholesterol particles. A library of nucleic acid sequences are tested for the desired binding characteristics and the sequences that are specific for lipoprotein cholesterol particles are isolated and replicated. Weintraub et al., WO 92/05285, and Gold et al., WO 91/19813 both disclose methods for the preparation of DNA and RNA sequence which are antigenic specific.

The VLDL-specific binding agent can be attached directly or indirectly to a solid support, for example, by absorption, adsorption, covalent coupling directly to the support or indirectly through another binding agent (such as an anti-antibody), or the like utilizing methods known in the art. The type of attachment or binding will typically be dependent upon the material composition of the solid support and the type of VLDL-specific binding agent used in the assay. For example, nitrocellulose, polystyrene and similar materials possess chemical properties that permit absorption or adsorption of proteins to a solid phase composed of this material. Other materials, such as, latex, nylon, and the like contain groups that permit covalent coupling of the VLDL-specific binding agent to the solid support. Chemical groups, such as, amines and carboxylic acids are coupled through the activation of the carboxylic acid group with, for example, carbodiimide compounds, to form an amide linkage. Other linking methods are well-known in the art particularly for coupling proteins to solid phases and one skilled-in-the-art can easily conceive of a variety of methods for covalently coupling the specific binding agent to the solid support. The solid support can take the form of a variety of materials, for example, the solid support may be in the form of a bead particle, a magnetic particle, a strip or a layered device.

b. Methods for Determining VLDL in a Fluid Sample

The present invention utilizes a VLDL-specific binding agent to form a binding complex with VLDL particles in a sample. In one embodiment, the method is performed by combining all components of the test mixture simultaneously, i.e. a VLDL-specific binding agent, a test sample, and any indicator reagent(s) for detecting VLDL and then determining the amount of apoB or cholesterol associated with VLDL. In a second preferred embodiment, a test sample is combined with a VLDL-specific binding agent and then separated from the binding agent-VLDL complexes formed before measuring the amount of apoB or cholesterol associated with VLDL in the complexes. More preferably, the VLDL particles are captured by a VLDL-specific binding agent directly or indirectly bound to a solid support. This methodology simplifies the separation of the resulting binding agent-VLDL complexes from the sample. Thus, in a preferred embodiment, the specific-VLDL particles of interest are separated from other lipoprotein particles (i.e. HDL, Lp(a), IDL and LDL cholesterol particles) in the sample before the determination of apoB or cholesterol associated with VLDL is made.

Separation of the binding-agent-VLDL complexes from the sample or more specifically from the other lipoprotein particles in the sample can be accomplished in a variety of ways. When the binding agent is coupled to a solid support, the solid support can be removed from the sample or the sample can be removed from the solid support. For example, when the solid support is a microtiter plate or another type of reaction well device, such as the devices described in U.S. Pat. No. 5,075,077 and 4,883,763, and U.S. patent application Ser. No. 523,629, the sample can be removed from the wells and the plate washed of any residual sample. When the solid support is a particle, such as a latex or magnetic particle, the solid support can be separated from the sample by filtration through a fiber matrix, such as the devices described in U.S. Pat. Nos. 4,552,839 and 5,006,309, U.S. patent applications Ser. Nos. 554,975, 611,235 and 425,651, and Fiore et al. (1988) Clin. Chem. 34: 1726–1723 or by attraction to a magnet followed by removal of the particles or the sample. Alternatively, the binding-agent-VLDL complexes can be separated or removed by filtration such as by the Ion Capture Methodology described in EP patents 0326100 and 0406473, both of which enjoy common ownership. These applications describe the use of ion capture separation, in which specific binding members used in an assay are chemically attached to a first charged substance and a porous matrix having bound thereto a second charged substance that binds to the first charged substance. A specific binding pair is formed and separated from the reaction mixture by an electrostatic interaction between the first and second charged substances. The specific binding member is preferably covalently coupled to the first charged substance. Examples of charged substances include anionic and cationic monomers or polymers, such as polymeric acids, e.g. polyglutamic acid, polyaspartic acid, polyacrylic acid and polyamino acids; proteins and derivative proteins, such as albumin; anionic saccharides, such as heparin or alginic acid; polycations, such as GafQuat™ L-200 and Celquat™ H-100. The art is replete with examples of solid supports, as well as techniques in the separation of samples from solid supports.

Alternatively, the methods of the present invention may be performed without the need for a separation step, as described in PCT Publication No. WO94/20636, published Sept. 15, 1994. PCT Publication No. WO94/20636 teaches genetically engineered proteins, such as hybrid enzymes and their preparation and use in quantitative and qualitative assays. In the method systems described, a hybrid enzyme is provided which comprises a starting enzyme and a foreign amino acid moiety that either replaces or is inserted into an amino acid sequence of the starting enzyme at a region close to the enzyme's active site. The foreign moiety may be either a first member of a specific binding pair or a linking moiety to which a ligand may be coupled or conjugated. In either case, the resulting hybrid enzyme exhibits the enzymatic activity of the starting enzyme. Furthermore, the foreign moiety of the hybrid enzyme can still bind to its corresponding specific binding pair member or to an anti-ligand and as a consequence of such binding, modulate or modify the activity of the hybrid enzyme. Thus, in an assay system comprising a hybrid enzyme, the enzymatic activity will change depending upon the presence or the amount of analyte in the test sample.

The hybrid enzyme provides a basis for assays to detect, (1) the presence or the amount of an antibody directly or (2) the presence or the amount of an antigen indirectly by competition for binding to a binding molecule. One assay system which utilizes a hybrid enzyme comprises the steps of (1) contacting a test sample containing an analyte of interest, a hybrid enzyme capable of binding to the analyte and a binding molecule of the analyte to form a reaction mixture; (2) contacting the reaction mixture with a substrate for the starting enzyme; and (3) monitoring the change, if any, in enzymatic activity of the hybrid enzyme. As an example, in the case of a VLDL-apoB competitive assay, the monoclonal antibodies of the present invention may be used as a binding molecule of the analyte (VLDL). Other assay formats, such as a direct assays are also envisioned.

The amount of apoB or cholesterol associated with VLDL in a fluid sample can be determined by a variety of assay formats. A preferred assay format, for example, is a sandwich assay. This method comprises contacting a test sample with a solid phase (hereinafter represented by the symbol "|-") to which at least one capture reagent (i.e. anti-analyte) is bound, to form a mixture. The mixture of test sample and capture reagent bound to a solid phase is incubated for a time and under conditions sufficient to allow |-capture reagent/analyte complexes to form. These complexes then are contacted with an indicator reagent comprising a second anti-analyte previously conjugated to a label. This second mixture is incubated for a time and under conditions sufficient for |-capture reagent/analyte/indicator reagent complexes to form. The presence of the |-capture reagent/analyte/indicator reagent complexes is determined by detecting the measurable signal generated. In such an assay, the capture reagent bound to the solid support may be, for example, a first antibody which binds to an antigen in the test sample, and the indicator reagent may be a second antibody which also binds to the antigen but at a site different from the first antibody. It is also within the scope of the present invention to use one antibody as a capture agent and a fragment of an antibody as an indicator reagent. In addition, sandwich-type assays may be configured in a reverse orientation to that described above, i.e. with an antigen serving as the capture reagent to test for the presence of antibody in a test sample. In this case, the indicator reagent is a second labeled antibody or fragment thereof which also binds to the complex of antigen/antibody bound to a solid support.

Detection of complexes formed in sandwich and other assays may be performed indirectly. In an indirect sandwich assay format, complexes of |-capture reagent/analyte/second capture reagent are formed, none of which are labeled. Instead, an ancillary specific binding member which binds to the second capture reagent acts as the indicator reagent. For example, when the second capture reagent is a mouse antibody to the analyte of interest, the complex of capture reagent/analyte/mouse antibody may be detected using an ancillary antibody which is labeled, such as labeled goat anti-mouse antibody. Furthermore, the use of biotin and antibiotin, biotin and avidin, biotin and streptavidin, and the like, may be used to enhance the generated signal in the assay systems described herein.

For purposes of illustration, the following sandwich formats may be utilized: in a first format, VLDL particles present in a plasma sample are specifically captured by a VLDL specific monoclonal antibody immobilized on a solid support. After removing the other lipoprotein particles, the apoB associated with the VLDL bound to the solid support is quantitated using an apoB specific monoclonal antibody or polyclonal antibody (which are labeled) as an indicator reagent. Since apoB is common to LDL, VLDL, IDL and Lp(a), any monoclonal or polyclonal antibody that cross reacts to the apoB of one or more of these lipoproteins is suitable as an indicator reagent (provided such antibody is not specific to the apoB of the specific lipoprotein, with the exception, of course, of VLDL). Such antibodies are well known to those of ordinary skill in the art (see, for example, WO 93/18067, published Sept. 16, 1993). Preferably, in these formats, the indicator reagent is labeled with an enzyme.

In addition to the foregoing sandwich assay formats, competitive assays are also contemplated by the invention. In one format, labeled VLDL may compete with the VLDL to be determined in a fluid sample for binding to a VLDL specific monoclonal antibody which has been immobilized on a solid support. In a second format, VLDL in the sample competes with VLDL attached to the solid support for binding by a labeled VLDL specific antibody. It is fully expected that other known assay formats may be advantageously adopted by the skilled artisan and these are within the scope of the invention, to be utilized with the unique antibodies herein set forth and described.

Another alternative is based on an immunochromatographic assay format (such as described in U.S. Pat. No. 4,954,452 and U.S. Pat. No. 5,229,073, for example) in which the lipoprotein particles in the test sample bind to a labeled VLDL binding agent. The resulting complexes then travel along a test strip by capillary action. The labeled Lp(a) complexes are then captured by a high affinity VLDL specific antibody immobilized on the test strip, followed by detection and measurement of the captured labeled VLDL complexes. Typically, the test strip is comprised of a porous or bibulous membrane and the result is determined by a visual readout of a detectable signal. Other test strip assay formats are also within the scope of the invention.

The use of scanning probe microscopy (SPM) for immunoassays also is a technology to which the monoclonal antibodies of the present invention are easily adaptable. In scanning probe microscopy, in particular in atomic force microscopy, in the capture phase, for example, at least one of the monoclonal antibodies of the invention is adhered to a solid phase and a scanning probe microscope is utilized to detect antigen/antibody complexes which may be present on the surface of the solid phase. The use of scanning tunneling microscopy eliminates the need for labels which normally must be utilized in many immunoassay systems to detect antigen/antibody complexes. Such a system is described in Publication No. WO 92/15709, published Sept. 17, 1992.

c. Methods for Determining VLDL-cholesterol

A VLDL specific binding agent can be used in an immunoassay method for the quantitation of VLDL-cholesterol in a fluid sample. This involves the specific capture of the VLDL particles in the sample by the VLDL-specific antibody immobilized on the solid support followed by quantitation of cholesterol in the captured VLDL particles by a cholesterol-binding agent which is coupled directly or indirectly to a label. The VLDL-cholesterol bound cholesterol binding agent is then quantitated by detection and measurement of the label. A variety of methods for quantitating cholesterol are available and are well known to those of ordinary skill in the art (see for example, WO 93/18067, published Sept. 16, 1993).

One embodiment of the method is illustrated by the following sandwich assay example. The method involves incubating the sample with a solid phase having an VLDL-specific binding agent, such as the monoclonal antibody 18-358-211 immobilized on a solid phase and preferably, blocking the remaining non-specific binding sites of the solid phase such as with bovine serum albumin or alkali-treated casein. VLDL particles are captured by the antibody on the solid phase. Digitonin or tomatine enzyme conjugates are then incubated with the solid phase. The conjugate binds to the cholesterol associated with the VLDL particles on the solid phase. The quantity or presence of enzyme bound to the solid phase or the quantity of unbound conjugate remaining after incubation with the solid phase is determined by incubation of enzyme substrate with the solid phase or the solution containing unbound conjugate. The presence of cholesterol associated with the captured VLDL particles is then determined from the presence of enzyme associated with the solid phase or a reduction of enzyme activity in the solution containing unbound conjugate as compared with the original conjugate solution added to the solid phase. The quantity of cholesterol associated with the captured VLDL particles is proportional to the quantity of enzyme associated with the solid phase or inversely proportional to the quantity of unbound conjugate.

In an alternative embodiment, after capture of a VLDL particle by a VLDL specific binding agent, the amount of cholesterol in or on a VLDL particle can be determined directly by a variety of methods. Such methods may be: chemical by using the Liebermann-Burchard method or modifications of their method; enzymatic by using a cholesterol-specific enzyme such as cholesterol oxidase; through the formation of a cholesterol-specific binding complex; or through the release of the cholesterol from VLDL followed by detecting the amount of cholesterol released using any of the above methods. One skilled-in-the-art may conceive of yet other methods of detection applicable to this method.

For purposes of illustration, a VLDL-cholesterol measurement can be made as follows: VLDL particles present in a plasma sample are specifically captured by an VLDL-specific monoclonal antibody immobilized on a solid support. After separating the solid support from the other unbound plasma lipoproteins, the cholesterol content of the bound VLDL particles is estimated by releasing the cholesterol and its esters with a detergent solution. A standard cholesterol assay reagent comprising cholesterol ester hydrolase, cholesterol oxidase and horseradish peroxidase is added. The liberated hydrogen peroxide is then quantitated using a Tinder dye reagent comprising of 4-aminoantipyrine and 3,5-dichloro-hydroxybenzenesulfonic acid similar to that described in the art (see Sidel et al. (1983) Clin Chem 29: 1075–1079). The cholesterol concentration in a given sample is quantitated on the basis of the color generation.

The measurement of VLDL-cholesterol can also be accomplished indirectly by removing all the other lipoproteins from the sample. The selective binding agents of a group of selected lipoproteins can be used to remove these lipoproteins from a sample, leaving behind substantially only one lipoprotein in the sample. Measurement of the cholesterol in the sample after this group of lipoproteins have been removed gives an indication of the amount of cholesterol present in the remaining lipoprotein. For example, selectively removing HDL, LDL, IDL and Lp(a) will essentially leave behind VLDL in the sample. Measurement of the cholesterol in the remainder of the sample will give an estimation of the VLDL-cholesterol present in the sample. The cholesterol levels associated with the other lipoproteins could be measured by simply changing the group of selected lipoproteins removed from the sample. Moreover, lipoprotein specific binding agents, such as antibodies, that are not selective for only one lipoprotein, such as an antibody that binds to both VLDL and LDL, but not Lp(a), can be used to remove the antibody cross-reacting lipoproteins (VLDL and LDL) in the measurement of cholesterol associated with a non-cross reacting lipoprotein (Lp(a)) using this indirect method.

This indirect approach can also improve the efficacy of lipoprotein specific binding agents, used in the direct measurement of a specific lipoprotein, that are not sufficiently selective for the lipoprotein of interest. By removing an antibody cross-reacting specific lipoprotein from the sample prior to specifically measuring the lipoprotein cholesterol of interest, the effect of such cross-reactivity is eliminated.

Moreover, the sequential removal and measurement of specific lipoprotein cholesterol levels from the same aliquot of sample permits the use of less selective lipoprotein binding agents in the measurement of lipoprotein cholesterol levels later in the sequence. For example, an antibody that binds to both VLDL and LDL could be used to selectively capture VLDL if the LDL present in the sample had previously been removed.

The following examples are illustrative of the invention and are in no way to be interpreted as limiting the scope of the invention as defined in the claims. It will be appreciated that one skilled-in-the-art can conceive of many other devices and methods for use of which the present inventive concepts can be applied. Throughout the entire specification, it is intended that citations to the literature, including patents and patent applications, are expressly incorporated by reference.

General Methodologies

1. Development of Monoclonal Antibodies against VLDL: Apolipoprotein CIII (Apo CIII) was used as immunogen to develop VLDL specific monoclonal antibodies. Apo CIII is primarily associated with VLDL as a major lipoprotein. It is also present in the HDL fraction as a minor component. Apo CIII contains 79 amino acid residues with a molecular weight of 9,000 (Brewer et al. (1974) J. Biol Chem 249: 4975). The objective of using Apo CIII as a target immunogen was to develop monoclonal antibodies that would interact with a preferred conformation dictated by VLDL and not by HDL.

a. Immunization: Six female 4–6 week old RBF/dn mice (Charles River, Wilmington, Mass.) were immunized with Apo CIII (Calbiochem, La Jolla, Calif.). The dose level was 25 $\mu$g in 0.1 mL of a 1:1 ratio of the Apo CIII solution in Freund's Complete Adjuvant (Difco Laboratories, Detroit, Mich.). The adjuvant emulsion route of injection was equally distributed interperitoneally and subcutaneous. The mice were given subsequent immunizations of Apo CIII on weeks three and five, 25 $\mu$g in 0.1 mL of a 1:1 ratio of Freund's incomplete Adjuvant. The adjuvant emulsion route of injection was equally distributed interperitoneally and subcutaneous. Three days prior to the fusion, mice were given an immunization of 25–50 gg Apo CIII in 0.9% saline by IV tail vein injection.

b. Sera Evaluation: Ten days following the third immunization, sera samples were taken by orbital vein puncture and analyzed for APO CIII specific antibody titer by enzyme immunoassay (EIA). Microtiter wells were coated with 100 microliters ($\mu$L) of 1 $\mu$g/mL Apo CIII in phosphate buffered saline (PBS) or 100 $\mu$l PBS and incubated at room temperature overnight. The following day the plates were blocked for 30 minutes with 200 $\mu$L per well of 3% bovine serum albumin (BSA) in PBS. After washing the plate, 50 μL of sera sample was added per well, at log 2 serial dilutions starting at a 1:100 dilution, and incubated 1 hour. The plates were washed and 50 μL of diluted goat anti-mouse IgG+M-HRPO (Kirkegaard and Perry Laboratories, Gaithersburg, MD), was added to the plate for a 30 minute incubation period. The plate was washed a final time and the color developed using o-phenyienediame.2HCl (OPD) (Abbott Laboratories, Abbott Park, Ill.). The relative intensity of optical density readings identified mouse numbers 1 and 5 to have the highest Apo CIII titer with minimal BSA background. Thus, these mice were selected for fusion ten weeks following the first immunization.

c. Fusion: On the day of fusion, the two mice were euthanized by cervical dislocation and a splenectomy was performed. Splenocytes were flushed out and washed in Iscoves's Modified Dulbecco's Medium (IMDM) (GIBCO, Grand Island, N.Y.) and centrifuged at 1000 rpm for 5 minutes. The splenocytes were combined with SP2/0 myeloma cells at a 1:1 ratio, washed in IMDM, and centrifuged. The supernatant was removed and 1 mL of 50% polyethylene glycol (PEG) (American Type Culture Collection, Rockville, Md.) was added to the pellet for one minute as the pellet was gently dispersed by tapping and swirling. Thirty milliliters of IMDM were added to the mixture and centrifuged as previously described. The supernatant was decanted and the pellet resuspended in IMDM with Hypoxanthine Aminopterin Thymidine (HAT) (GIBCO, Gaithersburg, Md.), 15% Fetal Bovine Serum (FBS) (Hyclone Laboratories, Logan, Utah), Origen Hybridoma Cloning Factor (Igen, Rockville, Md.), and Salmonella typhimurium mitogen (STM) (1% v/v) (RIBI Immunochem Research, Inc., Hamilton, Mont.). The fusion cells were plated into 96-well tissue culture plates at $3\times10^5$ cells per well. The fusion cells were given media changes by aseptically aspirating half the tissue culture supernatant and feeding with IMDM with 1% v/v HT (hypoxanthine and thymidine) Supplement (GIBCO, Gaithersburg, Md.), and 10% v/v FBS at days five and seven. The fusion protocol was referenced from Galfre, G. and Milstein, C. (1981), Preparation of Monoclonal Antibodies: Strategies and Procedures, Meth Enzymol 73:1–46.

d. Fusion Screening: The primary screening of the fusion occurred on day ten with confluent cultures. An EIA was performed in a similar manner to the assay used for testing sera samples. Microtiter wells were coated with 100 μL of 1 μg/mL Apo CIII in PBS and incubated at room temperature overnight. After washing and blocking as previously described, 50 μL of culture supernatant was added and incubated 1 hour. The plates were washed and goat anti-mouse HRPO conjugate was added to each well. The addition of conjugate was followed by washing and color development with OPD. Since the relative intensity of optical density readings identified hybrids 18-358, 18-571, 18-459 and 18-140 as having about three times that of negative control, normal mouse serum (NMS) (Organon Teknika-Cappel, Malvern, Pa.), these hybrids were expanded. Thereafter, they were selected for cloning because the optical density readings indicated specific binding to Apo CIII with minimal non-specific binding to BSA.

e. Hybrid Cloning: All four hybrids described above were cloned by limiting dilutions starting at 1–100, 10-fold to $10^6$. The cloning media used was IMDM with 10% v/v FBS and 1 % v/v HT Supplement. A 200 μL cell suspension was added to each of the 96 wells in the tissue culture plate.

f. Clone Selection: The clone screening occurred on day ten with confluent cultures. Clones were selected based on EIA reactivity specific to Apo CIII with minimal nonspecific binding to a BSA background. The EIA screening protocol used was as described above.

g. Isotypes: The isotypes of the monoclonal antibodies secreted from the cell lines identified as 18-358-211, 18-571-312, 18-459-172 and 18-140-196 were determined on a Isotype AL-STAT kit (Sargstat Medical Corp., Menlo Park, Calif.). Assays of each were performed according to the vendor recommendations and indicated that 18-150-196 was IgG2b and the other three monoclonal antibodies were IgG1.

"A murine hybridoma which produces Mab 18-358-211 has been deposited under the terms of the Budapest Treaty in the American Type Culture Collection, 10801 University Blvd, Manassas, Va., 20110-2209, USA on Aug. 26, 1997, and has been accorded accession number ATCC HB-12393. The deposit is provided for convenience only, and is not required to practice the present invention in view of the teachings provided herein."

h. Antibody Production: Cell lines 18-358-211, 18-571-312, 18-459-172 and 18-140-196 were expanded in volume with IMDM with 5% v/v Fetal Clone Serum (Hyclone Laboratories, Logan, Utah) in tissue culture flasks at a cell density between $1\times10^4$ cells/mL and $5\times10^5$ cells/mL until they could be expanded into roller bottles. The roller bottle cells were allowed to grow for maximum antibody production, i.e. normally until viability fell below 5%.

i. Antibody Purification: Cultures were removed from roller bottle incubators and cells were allowed to settle for three days at 4–8° C. Cell supernatants were filtered through 0.45 μm filters and concentrated approximately 20× on an Amicon Concentrator (Amicon Corp., Beverly, Mass.). Concentrated supernatants were filtered through an additional 0.45 μm filter. These materials were then purified by Protein A-Sepharose column chromatography as described by Ey et al., (1978), Inmunochem 15: 429–436. The purified and dialyzed antibody was tested for Apo CIII reactivity by EIA as previously described.

2. Evaluation of Monoclonal Antibodies: The following methods were used to evaluate the antibodies.

a. Specificity of the Mabs in a Direct Binding ELISA using Lipoprotein Coated Microtiter Plates: Lipoprotein fractions (LDL, HDL, VLDL, and IDL) purified by ultracentrifugation (see Example 2, infra) were coated on separate wells of a Maxisorb Nunc Immuno Plate as follows: one hundred microliters (100 μL) of each lipoprotein fraction at a lipoprotein-cholesterol concentration of about 1 μg/mL in 20 mM phosphate buffered saline at pH 7.0 (PBS) was dispensed into separated wells of the microtiter plate. The plate was incubated at 37° C. for one hour and then washed five times with PBS containing 0.05% (v/v) Tween 20 (PBS-Tween 20). Non-specific binding sites were blocked with 200 μL of 10% (v/v) fetal bovine serum (FBS) in PBS at 37° C. for one hour and the plate then washed five times with PBS-Tween 20. Each monoclonal antibody was diluted in 3% (v/v) FBS in PBS to a final antibody concentration of about 2 μg/mL and the diluted monoclonal antibody solutions were serially diluted on the plate. After incubation at 37° C. for one-half hour, the plate was washed five times with PBS-Tween 20. Thereafter one hundred microliters (100 μl) of horseradish peroxidase (HRPO) labeled goat anti-mouse IgG (obtained from Kirkegaard and Perry Laboratories, Md.), diluted in 3% FBS in PBS to a final concentration of about 1.25 μg/mL, were added to each reaction well and the plate was incubated at 37° C. for one half hour. The plate was then washed eight times with PBS-Tween 20. One hundred microliters (100 μl) of freshly prepared HRPO substrate solution, containing one o-phenylenediamine (OPD) tablet per five milliliters (5 mL) of citrate buffer at pH 6 (both available from Abbott Laboratories, Abbott Park, Ill.) were added to each well. The color reaction was stopped after five minutes by adding 100 μl of 1 N $H_2SO_4$ to the reaction wells. An absorbance reading of each reaction well was then obtained with a Bio-Tek microplate reader at 490 nm. Typical binding curves for each lipoprotein tested with monoclonal antibody 18-358-211 are shown in FIG. 1. A summary of test results are presented in Table 1 which shows the binding effeciencies of the lipoproteins relative to LDL at an antibody concentration of about 0.1 μg/mL. As Table 1 shows, none of the four monoclonal antibodies bound to LDL and IDL. Furthermore, antibody 18-358-211 showed no cross-reactivity with HDL. The other three monoclonal antibodies showed very weak cross reactivity with HDL (3–8%).

TABLE I

Binding of Monoclonal Antibodies to Lipoproteins on a Solid Phase

| Mab* | % Cross-reactivity | | | |
|---|---|---|---|---|
| | VLDL | LDL | IDL | HDL |
| 18-571-312 | 100 | 0 | 0 | 5 |
| 18-140-196 | 100 | 0 | 0 | 8 |
| 18-459-172 | 100 | 0 | 0 | 3 |
| 18-358-211 | 100 | 0 | 0 | 0 |

Figure 2:
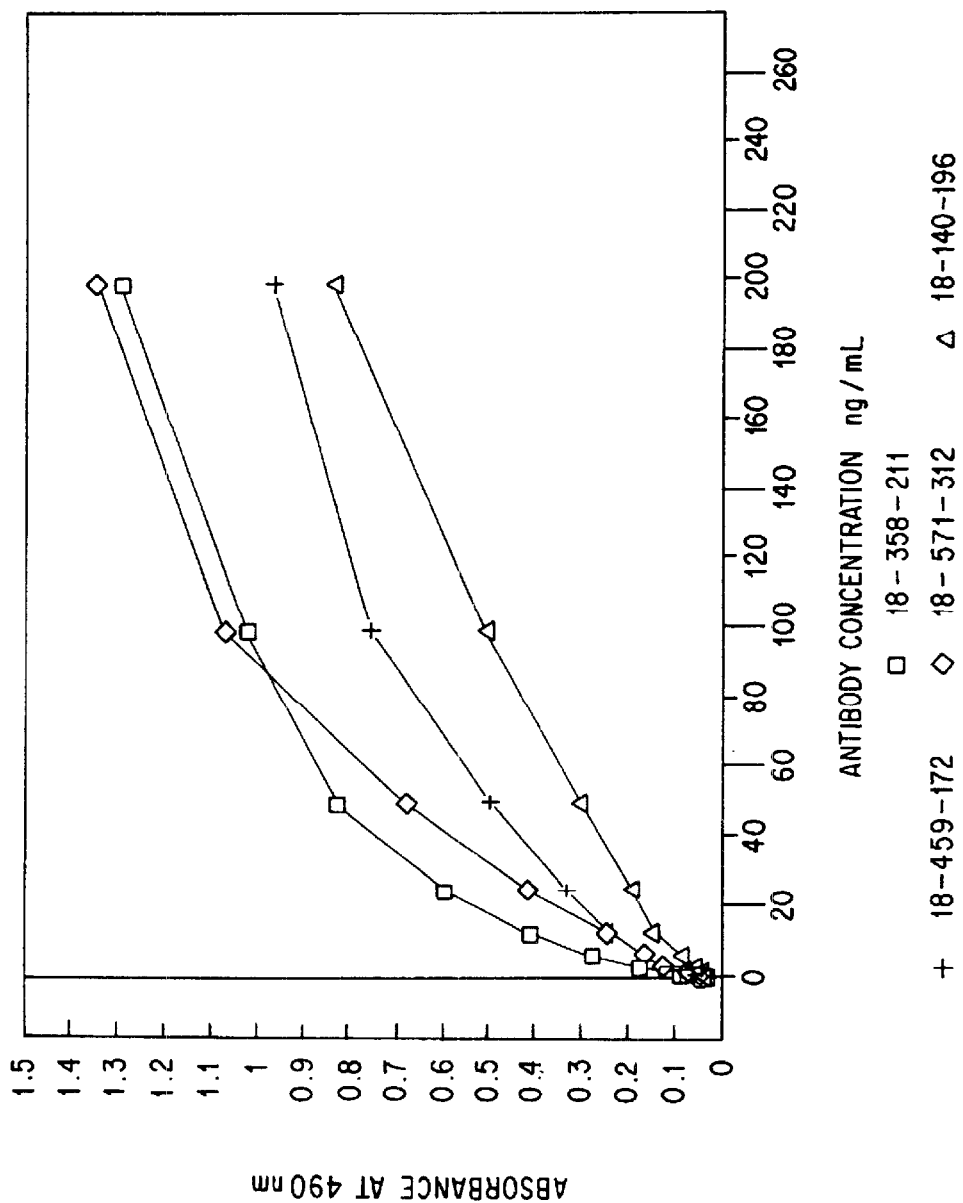
FIG. 2: Antibody titer plots of four monoclonal antibodies obtained by incubating antibodies with VLDL bound to the microliter plates and measuring the binding of antibodies to VLDL by an ELISA.
Figure 3:
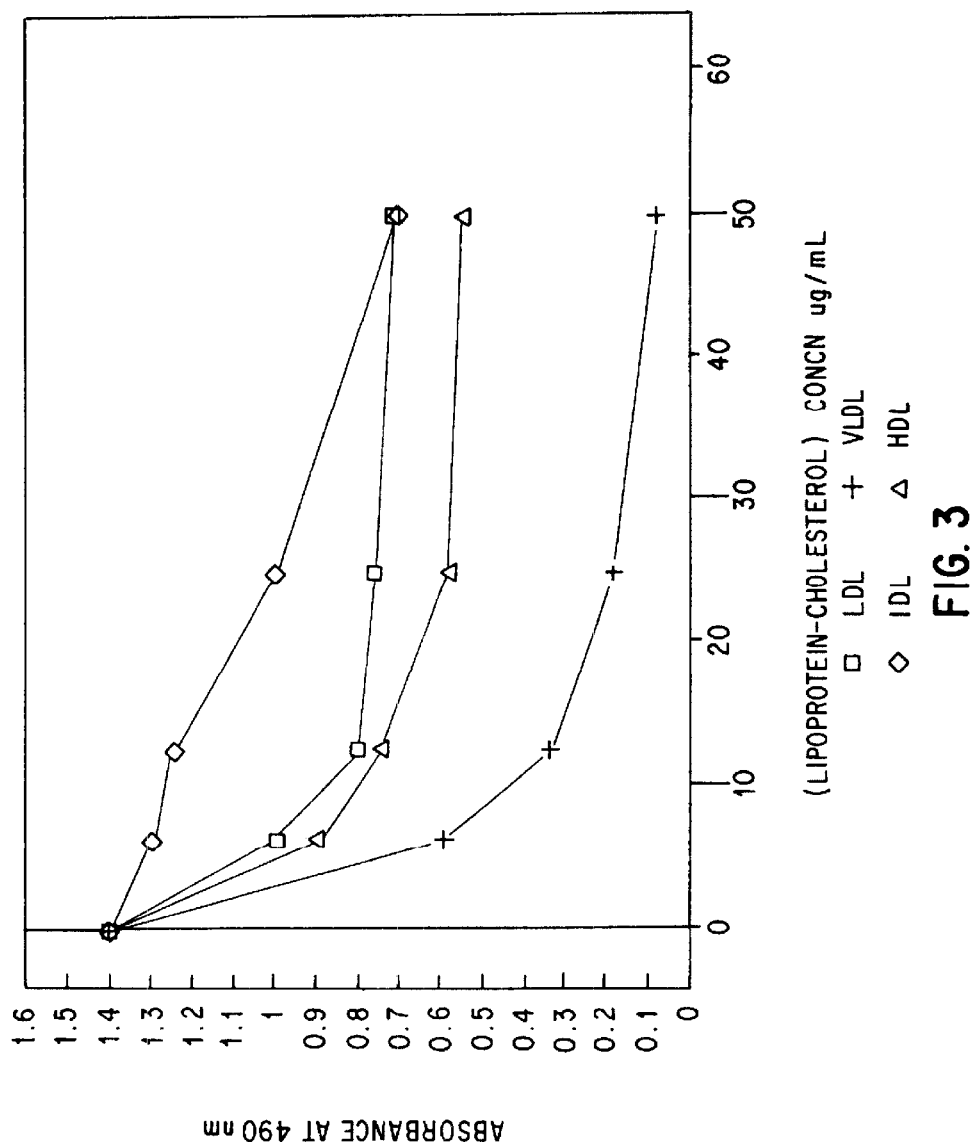
FIG. 3: Typical competitive binding curves of the monoclonal antibody 18-358-211 obtained by pre-incubating the antibody with a lipoprotein, adding the mixture to the microtiter plate with VLDL bound to the plate reaction wells and measuring the antibody bound to the VLDL by an ELISA.

*At 0.1 μg/mL antibody concentration b. Specificity of the Mabs to VLDL in Competitive Assays using Lipoprotein Coated Microtiter Plates: The specificities of the monoclonal antibodies were determined by competitive binding of the monoclonal antibodies to the other lipoproteins in microplate wells coated with VLDL. The VLDL-coated plates were prepared as described previously (see section 2a above). Each monoclonal antibody was diluted with 3% (v/v) FBS in PBS to a concentration that was two times the monoclonal antibody concentration at 50% VLDL-binding as determined from the binding curves generated in Section 2a above. The binding curves of the four monoclonal antibodies curves are shown in FIG. 2. Purified lipoprotein samples were diluted in PBS starting at 50 μg/mL cholesterol concentration. Fifty microliters (50 μL) of each lipoprotein solution were then serially diluted with PBS in reaction wells blocked by 10% (v/v) FBS in PBS. To each of these wells were added 50 μL of the diluted monoclonal antibody solutions. The monoclonal antibody-lipoprotein mixtures were incubated at room temperature for one-half hour on a rotator at 100 rpm. The contents from each well were then transferred to VLDL-coated reaction wells and the plates were incubated at 37° C. for one-half hour. The amount of monoclonal antibody bound to the VLDL-coated reaction wells was measured according to the method described in Section 2a above. Typical competitive binding curves are shown in FIG. 3. A summary of the test results are presented in Table 2. The cross-reactivities were determine at 66.67% inhibition of binding by a competing lipoprotein using the following equation:

Cross-reactivity (%)=Amount needed by VLDL×100 Amount needed by competitor

The results seen in Table 2 indicate extensive binding of monoclonal antibody 18-571-312 to HDL in contrast to the binding curves obtained in Section 2a above. In Section 2a, this monoclonal antibody shows no binding to HDL, whereas in the inhibition assay, both VLDL and HDL show equal affinity for this monoclonal antibody. This result indicates that the affinities of some monoclonal antibodies toward lipoproteins differ depending on whether the reaction is performed with a solid phase (FIG. 2) or in a fluid phase (FIG. 3).

TABLE 2

Competitive Binding of Monoclonal Antibodies by ELISA

| Mab* | % Cross-reactivity | | | |
|---|---|---|---|---|
| | VLDL | LDL | IDL | HDL |
| 18-571-312 | 100 | 0 | 0 | 100 |
| 18-140-196 | 100 | 0 | 0 | 0 |
| 18-459-172 | 100 | 0 | 8 | 4 |
| 18-358-211 | 100 | 0 | 0 | 0 |

*At 66.67% inhibition of binding c. Specificity of the Mabs in a Direct Binding ELISA using Antibody Coated Microtiter Plates: Monoclonal antibodies were coated on wells of microtiter plates as follows: Antibodies were diluted in PBS to a concentration of 10 μg/mL. One hundred microliters (100μl) of each antibody solution were dispensed into separate reaction wells and incubated at room temperature on a rotator at 100 rpm for two hours. The plates were then washed five times with PBS-Tween 20 and blocked with 200 μL of 10% EBS in PBS by incubation at 37° C. for one hour. The plates were then washed five times with PBS-Tween 20.

Figure 4:
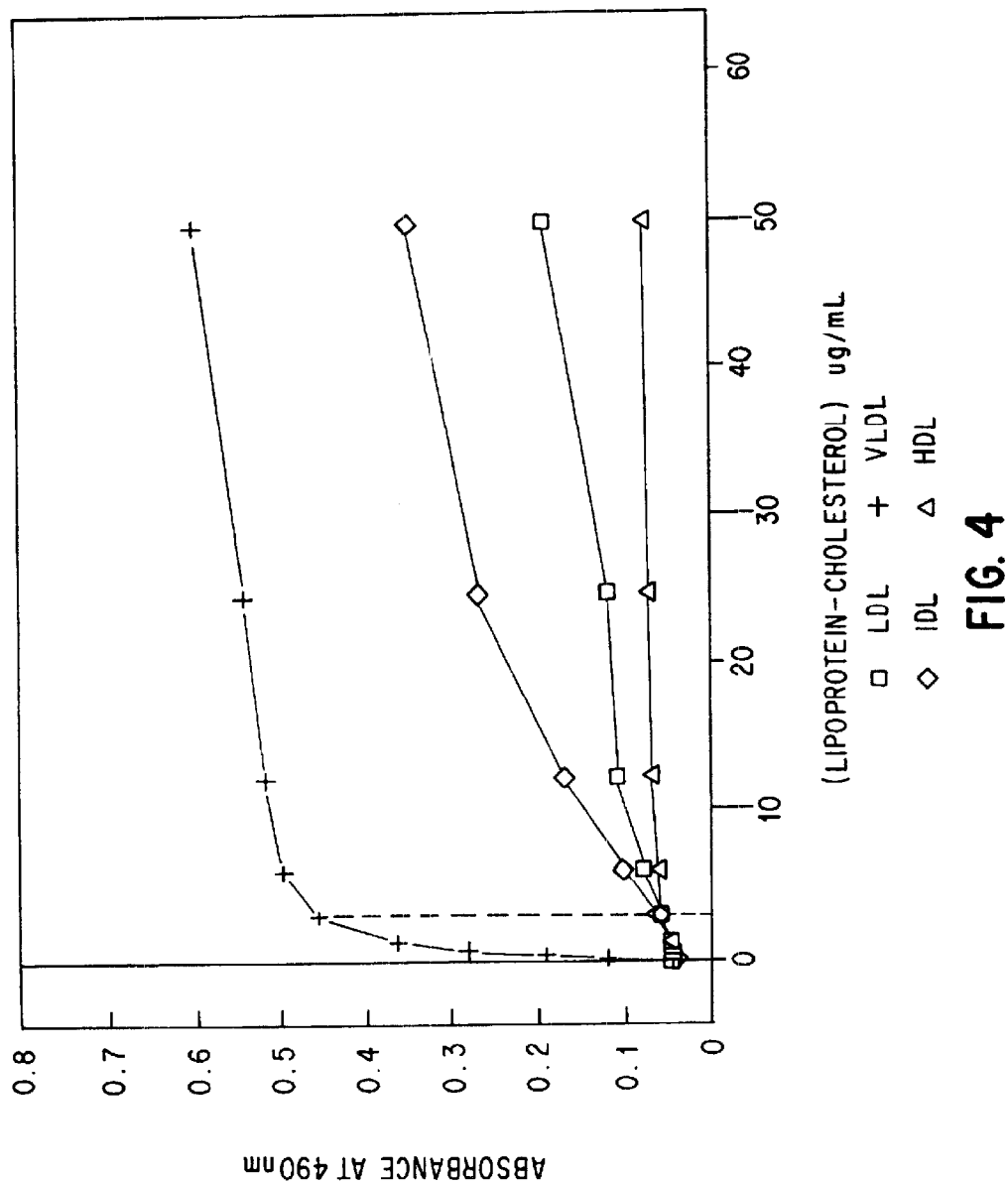
FIG. 4: Typical titration of LDL, VLDL, HDL, and IDL with the monoclonal antibody 18-358-211 obtained by incubating the lipoproteins with the antibody bound to the microtiter plates and measuring the binding of the lipoproteins to the antibody by an ELISA.
Figure 5:
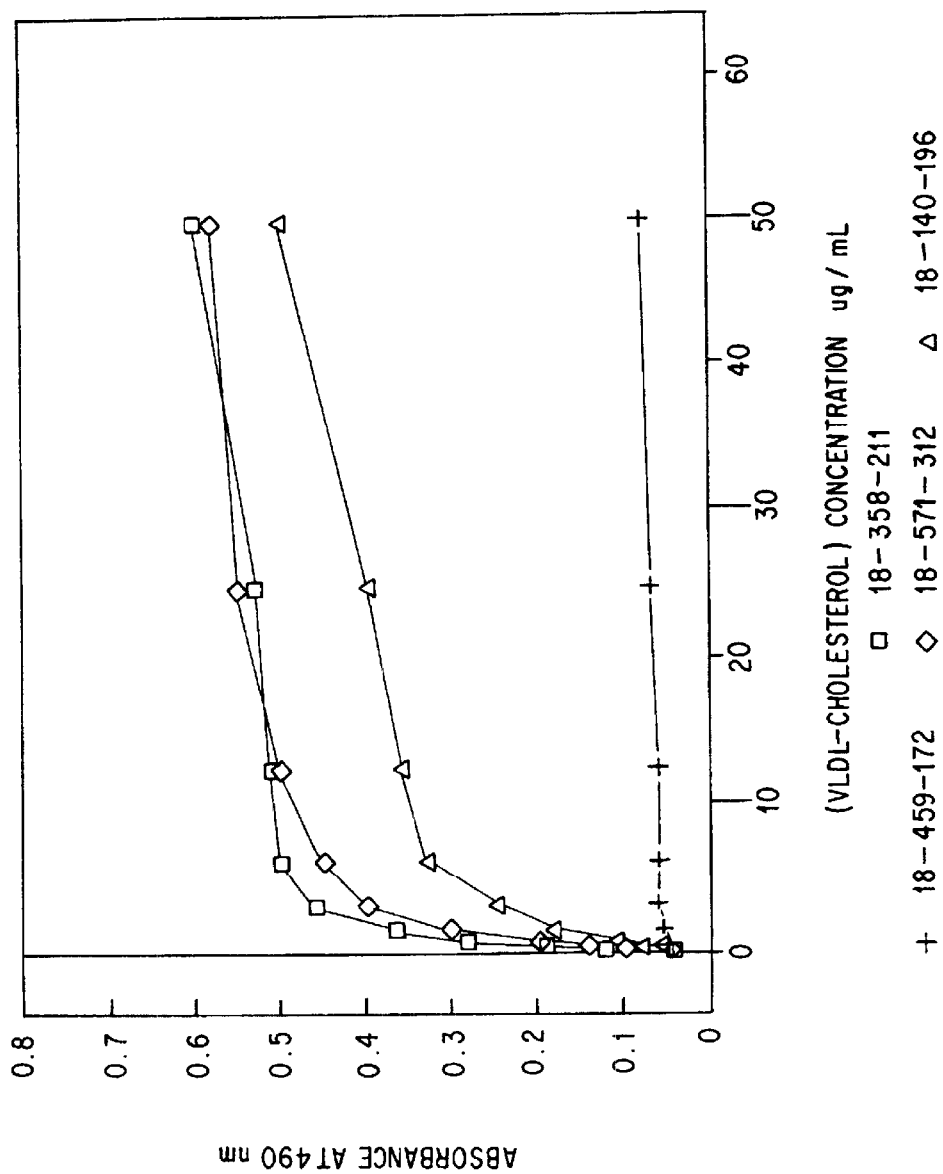
FIG. 5: Titration of VLDL with four monoclonal antibodies obtained by incubating VLDL with monoclonal antibodies bound to the microtiter plates and measuring the binding of VLDL to the antibodies by an ELISA.

Each monoclonal plate was then serially diluted with VLDL, LDL, IDL, and HDL in PBS, starting with a lipoprotein-cholesterol concentration of 5 mg/dL cholesterol, so that each well contained a total of 100 μl of solution. After incubation at 37° C. for one-half hour, the plates were washed five times with PBS-Tween 20. One hundred microliters (100 μL) of 0.5 μg/mL anti-ApoB-HRPO or 1 μg/mL anti-HDL-HRPO conjugate (prepared according to Example 3) in 3% FBS in PBS were added to the respective wells. LDL-, VLDL- and IDL- containing wells received anti-ApoB conjugate and HDL-containing wells received anti-HDL conjugate. After incubation at 37° C. for one-half hour, HRPO substrate was added and the absorbance measured as described in Section 2a above. FIG. 4 shows typical binding curves of lipoproteins for the monoclonal antibody 8-358-211 (coated on a solid phase) and FIG. 5 shows a comparison of the binding of VLDL to the four monoclonal antibodies. A summary of test results are presented in Table 3 which shows the binding efficiencies of the lipoproteins relative to VLDL at an antibody concentration of 3.13 μg/mL.

TABLE 3

Binding of Lipoproteins to Mabs on a Solid Phase

| Mab* | % Cross-reactivity | | | |
|---|---|---|---|---|
| | VLDL | LDL | IDL | HDL |
| 18-571-312 | 100 | 8 | 5 | 5 |
| 18-140-196 | 100 | 35 | 0 | 7 |
| 18-459-172 | 0 | 100 | 0 | 3 |
| 18-358-211 | 100 | 5 | 7 | 5 |

*3.13 μg/mL lipoprotein-cholesterol concentration

As seen in Table 3, monoclonal antibodies 18-358-211 and 18-571-312 showed minimum cross-reactivity (less than 10%) with LDL, BDL and HDL. In contrast, Mab 18-459-172 bound to LDL only and Mab 18-140-196 showed high reactivity (35%) with LDL.

The selection of a preferred monoclonal antibody that could be used in the VLDL capture assay of the present invention was based on the consistency of the specificity results in the direct titration assay (as exemplified in Section 2a and Table 1), inhibition assay (as exemplified in Section 2b and Table 2) and also by the direct binding of lipoproteins to monoclonal antibodies immobilized on a solid phase (as exemplified in Section 2c and Table 3). Monoclonal antibody 18-358-211 was the only Mab which performed consistently in all three experiments described above and therefore was selected in developing the VLDL-cholesterol assays.

3. Imobilization of Monoclonal Antibody to Solid Phase: An assay system was designed to selectively capture VLDL particles on an antibody coated solid phase and assay for cholesterol in the bound VLDL. Since cholesterol or other lipids associated with lipoproteins are very hydrophobic, it is desirable to use solid phases which are hydrophillic in a solid phase assay for cholesterol. Moreover, the solid phase should have a high binding capacity and be non-porous to avoid preferential inclusion of lipoproteins in a porous solid phase. Also, in the case where antibody is to be immobilized on a solid phase, the activity and the orientation of the immobilized antibody must be substantially preserved. CNBr-activated Sepharose 4B (Pharmacia LKB) was used to demonstrate the feasibility of an VLDL-specific cholesterol assay. However, other hydrophilic solid phases, such as carbolink hydrazide agarose beads (Pierce Chemicals, Rockford, Ill.), Sulfolink coupling agarose beads (Pierce Chemicals), Trisacryl (IBF), HEMA-epoxy Bio Gel, HEMA vinylsulfone Bio Gel (Altech Associates, Deerfield, Ill.), glycosylated silica gel or control porous glass, hydrophilic latex beads, and other like cellulosic materials can also be used.

4. Evaluation of Antibody Immobilized Solid Phases: The antibody immobilized solid phases were evaluated in terms of their binding efficiencies by incubating the solid phases with two plasma samples and then determining the amount of VLDL bound by measuring the amount of cholesterol in the bound solid phases.

Figure 6:
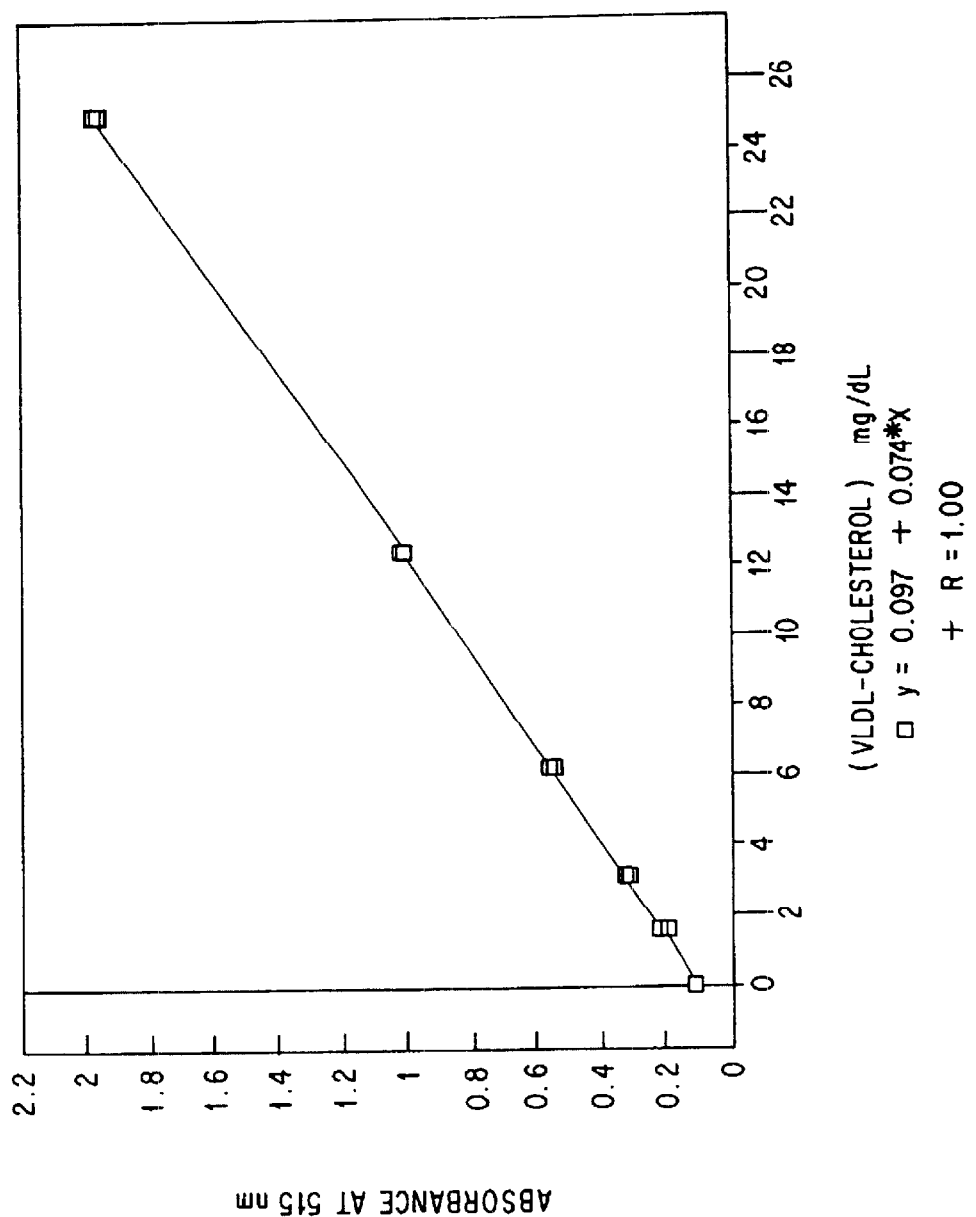
FIG. 6: A typical cholesterol standard curve for a specific VLDL-cholesterol immunocapture assay of this invention.

The protocol for a preferred lipoprotein capture assay is described in Example 8. The assay was performed using reagents prepared as described in Example 4. A typical cholesterol standard curve is shown in FIG. 6.

The efficiency of VLDL capture on a Sepharose 4B matrix having monoclonal 358-211 bound thereto is shown in Table 4.

TABLE 4

Efficiency of VLDL Capture on Mab 18-358-211-Sepharose Matrix

| Mab Matrix* ($\mu$L) | Amount VLDL-Chol (mg/dL) | Plasma Sample No. | Amount of Plasma ($\mu$L) | % VLDL Captured |
|---|---|---|---|---|
| 25 | 60 | 9 | 10 | 98 |
| 25 | 60 | 9 | 20 | 96 |
| 50 | 60 | 9 | 10 | 100 |
| 50 | 60 | 9 | 20 | 98 |
| 25 | 50 | 11 | 10 | 100 |
| 25 | 50 | 11 | 20 | 100 |
| 50 | 50 | 11 | 10 | 100 |
| 50 | 50 | 11 | 20 | 98 |

*Antibody-Matrix Concentration = 4.28 $\mu$g/mL

As Table 4 shows, under all conditions tested, at least 96% of VLDL particles were captured from plasma sample nos. 9 and 11, even using a 25 $\mu$L matrix volume. In developing the VLDL-cholesterol immunocapture assay, a 50 $\mu$L matrix volume and 10 $\mu$L plasma volume were used. As also seen in Table 4, the binding capacity of a 50 $\mu$L matrix at least two-fold of 60 mg/dL VLDL-cholesterol concentration if a 10 $\mu$L plasma volume is used, i.e. using this methodology, a VLDL-cholesterol concentration up to 120 mg/dL can be completely captured.

5. VLDL-Immunocapture Assay: The protocol for a VLDL-immunocapture assay is described in Example 9. The VLDL-cholesterol concentrations were correlated with a reference ultracentrifugation method described in Example 7. One hundred subjects whose liquid profiles are shown in Table 5 were used in this study. Eighty-seven normal subjects, nine patients with coronary heart disease who were under lipid lowering drug treatment (indicated by asterisk *) and four diabetic patients (indicated by double asterisks **) participated in this study.

Figure 7:
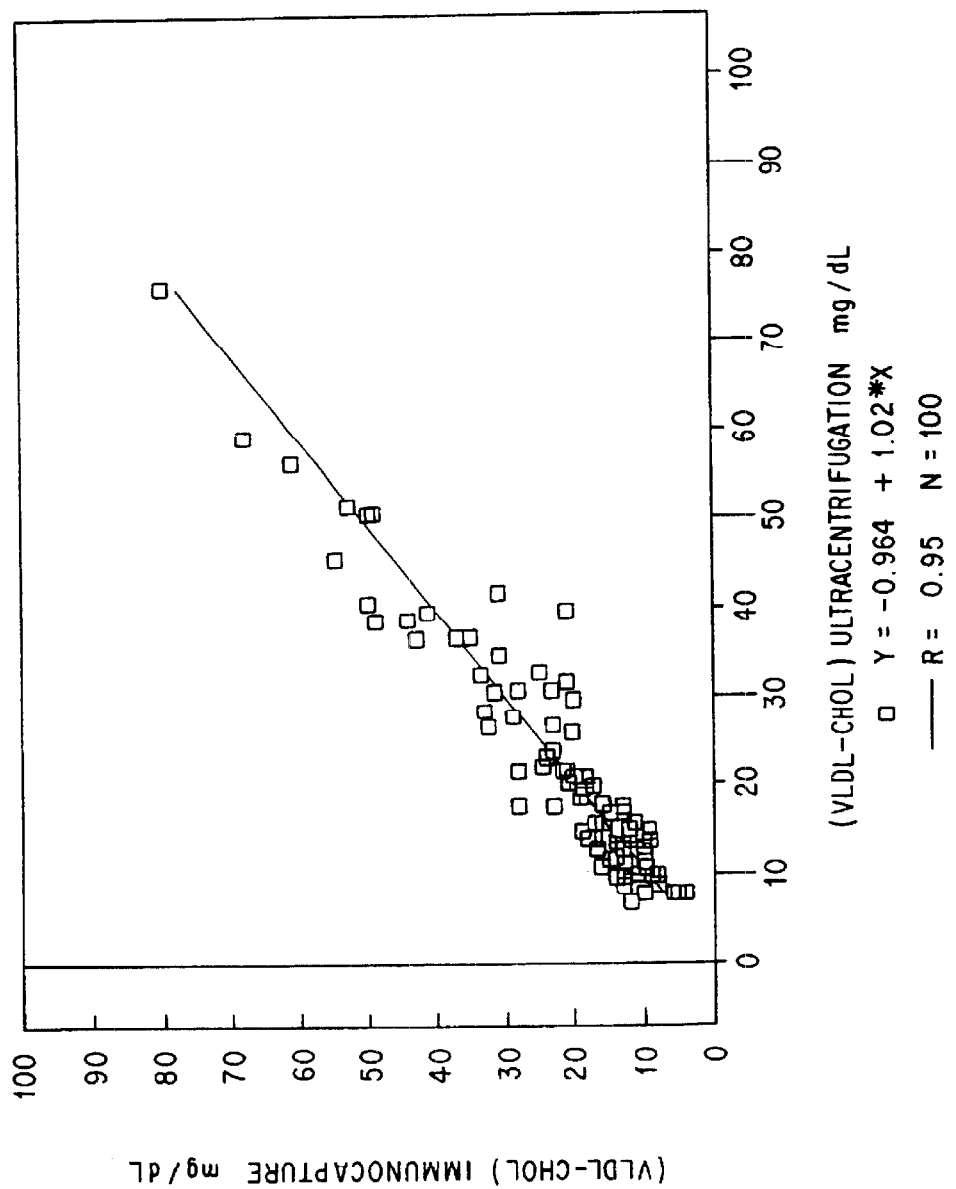
FIG. 7: A correlation curve for VLDL-cholesterol measurements by the immunocapture assay using the monoclonal antibody 18-358-211 -Sepharose and the ultracentrifuge method.

The VLDL-cholesterol concentrations determined by the ultracentrifuge method and the immunocapture assay using monoclonal antibody 18-358-211-Sepharose are presented in Table 6. The correlation between the ultracentrifuge method and the immunocapture assay is shown in FIG. 7. The correlation coefficient (r) was 0.95 with an intercept of −0.964 and a slope of 1.02. The results demonstrated that monoclonal antibody 18-358-211 is capable of capturing all VLDL particles of heterogeneous sizes (Musliner et al. (1986) Arteriosclerosis 6: 79–87).

6. Cholesterol Binding Agents a. VLDL-cholesterol standards: A plasma sample with a known VLDL-cholesterol concentration as determined by the ultracentrifuge method was used to generate a VLDL-cholesterol standard curve. Standards for VLDL- cholesterol concentrations within the range of about 20 mg/dL and 30 mg/dL were prepared by diluting the plasma sample with 1% alkali-treated casein in 20 mM phosphate buffered saline (PBS) at pH 7.4.

b. Preparation of Digitonin-Peroxidase Conjugates: Digitonin (2.5 mg/mL in water) (water soluble containing 50% digitonin and sodium deoxycholate commercially available from SIGMA Chemical Company, St. Louis, Mo.) was oxidized with sodium meta-periodate by adding a solution of periodate (1.68% w/v in water) to the digitonin solution to a final concentration of 0.02 M periodate (Tschesche and Wulff (1963) Tetrahedron 19: 621–634). The mixture was stirred at 4° C. for one hour and then dialyzed against 20 mM phosphate buffered saline (PBS), pH 8.0, at 4° C. overnight. A solution of 0.25 M ethyienediamine in 20 mM PBS, pH 8.0, was added to the oxidized digitonin solution to a final concentration of 0.05 M ethylenediamine and incubated at 4° C. The mixture was then reduced by two additions of 100 $\mu$L of a sodium borohydride solution per 30 mg of digitonin, after 30 minutes and after 60 minutes. After incubating at 4° C. for two hours, the mixture was dialyzed against 0.01 M carbonate buffer, pH 9.5, at 4° C. overnight.

Five milligrams (5 mg) of horseradish peroxidase (HRPO, 155 Ku/mg, commercially available from Amano International Enzyme Co., Troy, Va.) was dissolved in water to a final concentration of 4 mg/mL HRPO. The HRPO was oxidized by adding a freshly prepared solution of 0.2 M sodium meta-periodate (50 $\mu$L/milligram of HRPO) and incubating the mixture in the dark at room temperature for 20 minutes. The mixture was then dialyzed against 2 liters of 1 mM acetate buffer, pH 4.5, at 4° C. for 4 hours.

Figure 9:
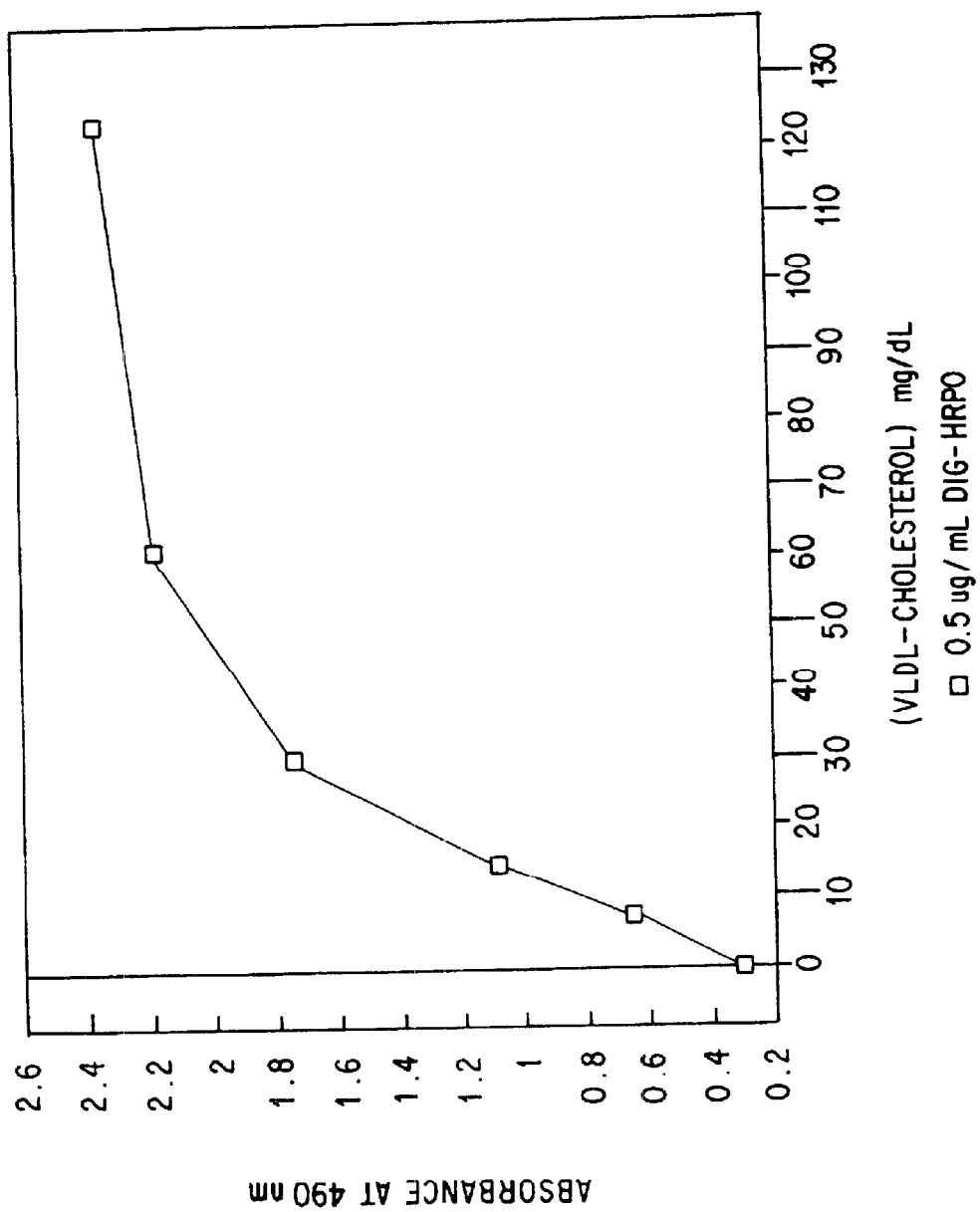
FIG. 9: A typical calibration curve plot of VLDL-cholesterol concentration versus absorbance using the immunoassay method of Example 10.
Figure 10:
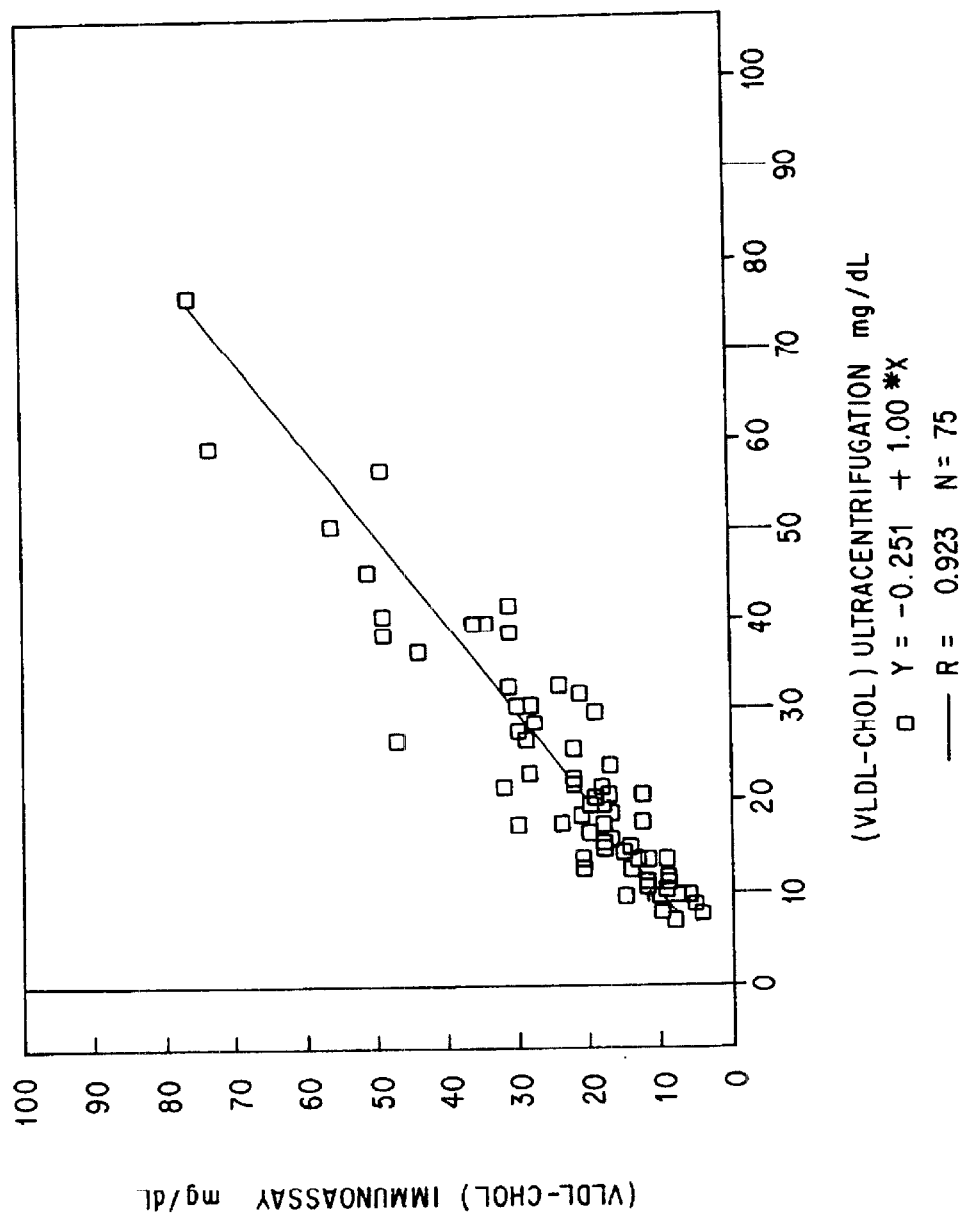
FIG. 10: A correlation curve for VLDL-cholesterol measurements by the immunoassay method using the monoclonal antibody 18-358-211 and ultracentrifuge method.

The ethylenediamine derivatized digitonin solution and the oxidized HRPO solution were mixed in digitonin:HRPO weight ratios of 1:5. To the reaction was added 0.2 M carbonate buffer, pH 9.5 (50 $\mu$L buffer/mg digitonin), and the pH was adjusted to 9.5 as necessary. The reaction mixture was stirred in the dark at room temperature for two hours and 100 µL of sodium borohydride solution (4 mg/mL in water) was added to the reaction. After incubating for two hours at 4° C., the reaction was dialyzed against 20 mM PBS, pH 7.4, at 4° C. overnight. To each mixture was added fatty-acid free bovine serum albumin (to a final concentration of 5 mg/mL). The solution was then sterile filtered through a 0.22 µm filter (Coaster Labs) and stored at −20° C.

c. Anti-APO CIII Coated Plates: VLDL specific Mab 18-358-211 was diluted in 20 mM PBS, pH 7.4, to a final concentration of 15 µg/mL. One-hundred microliters of the solution was added to each well of Maxisorb Nunc Immuno plates (Nalge-Nunc International, Naperville, Ill.) and incubated at room temperature with gentle shaking for two hours. The plates were washed five times with PBS-Tween and then blocked with 200 µL of 5% BSA in 20 mM PBS by incubation at 37° C. for one hour. The plates were stored at 4° C. with plastic sealers. Before use, the plates were washed five times with PBS-Tween (if HRPO conjugates were to be used in the assay) or TRIS-Tween (for assays utilizing AP conjugates).

d. Generation of VIDL-Cholesterol Standard Curves: VLDL-cholesterol standards (100µL/well, in duplicate) were incubated in the monoclonal antibody coated plates (Section 6c above) at 37° C. for one hour. After washing the plates five times with PBS-Tween, 100 µL of digitonin-HRPO conjugate at 0.5 µg/mL in 1 % casein in PBS was added to each well and incubated at 37° C. for one hour. The plates were washed with PBS-Tween eight times. OPD (100 µL of standard solution prepared from one OPD tablet/10 mL citrate buffer, pH 6; both commercially available from Abbott Laboratories, Ill.) was added to the wells. After incubation for 10 minutes, the color reaction was stopped with 100 µL of 1 N $H_2SO_4$. The plates were read at 490 nm on a microplate reader (Bio-Tek Instruments, Wingoski, Vt.). Standard curves (absorbance vs VLDL-cholesterol concentration) were generated from the results. A typical calibration curve plot of VLDL-cholesterol concentration by the sandwich assay is shown in FIG. 9.

e. Evaluation of VLDL-Cholesterol in Plasma Samples: Plasma samples in ethylenediaminetetraacetic acid (EDTA) were collected from normal individuals and patients and frozen at −20° C. until use. Thawed samples were not used after two days storage at 4° C. The samples were diluted 125-fold in 1% casein in PBS and assayed for VLDL-cholesterol according to the procedure of Section 6d above with the modification that the diluted samples were used in place of the standards. Along with the samples, standards were also assayed in duplicate as described in Section 6d. For each microtiter plate, a standard curve was generated and the values of the samples were determined using a point-to-point fitted computer program. Seventy five subjects (Nos. 1–75 in Table 5) were used in this study. The VLDL-cholesterol concentrations determined by the ultracentrifuge method and the assay of the present invention using monoclonal antibody 18-358-211-Sepharose and digitonin-HRPO are presented in Table 6. The correlation between the ultracentrifuge method and the sandwich assay is shown in FIG. 10. The correlation coefficient (r) was 0.923 with an intercept of −0.251 and a slope of 1.00. The results demonstrate that Mab 18-358-211 is capable of capturing VLDL particles of heterogeneous sizes as demonstrated in the immunocapture assay of this invention.

EXAMPLE 1
Preparation of Lipoprotein Fractions
Blood samples from normal fasting subjects were collected into ethylenediamine-tetraacetic acid (EDTA) and the red blood cells were removed by centrifugation. The plasma samples were then analyzed for Lp(a) using a TERUMO ELISA kit (Terumo Medical Corp., Elkton, Md.). Plasma samples containing less than 1 mg/dL Lp(a) cholesterol were selected for the purification of VLDL, IDL, LDL and HDL. Lipoprotein subtractions were prepared in a Beckman Ultracentrifuge with a SW 40 Ti rotor by successive ultracentrifugation at 4° C. (Havel et al. (1955) J Clin Invest 4: 1345–1355). VLDL was collected at a density of about 1.006 g/mL; IDL was collected at a density range of about 1.006–1.019 g/mL; LDL was collected at a density range of about 1.019–1.050 g/mL; and HDL was collected at a density range of about 1.080–1.255 g/mL. All fractions were isolated by the tube-slicing technique (Beckman Instruments, SPINCO Division, Palo Alto, Calif.). The lipoprotein fractions were dialyzed exhaustively against 0.15 M sodium chloride containing 0.1 % EDTA and 0.1 % sodium azide, pH 7.4 at 4° C. The IDL, LDL and HDL fractions were sterile filtered through 0.2 µm membrane filters (Nalgene) and VLDL through a 0.45 µm membrane filter (Nalgene) and stored at 4° C. The purity of each lipoprotein fraction was evaluated by electrophoresis under non-denaturing polyaccrylamide gradient gel electrophoresis (Lefevre et al. (1987) J Lipid Res 28: 1495–1509). Gradient slab gels of 2–16% and 4≧30% and electrophoresis apparatus GE-24 (Pharmacia LKB) were used in the analysis. The lipoprotein fractions containing no cross-contamination were used in the studies.

EXAMPLE 2
Preparation of Peroxidase Conjugates of Anti-ApoB and Anti-Hdl Antibodies Mab 1-1182-137, developed at Abbott Laboratories using intact LDL particles as an immunogen, was used. This monoclonal antibody shows equal affinity with LDL, VLDL, and IDL in direct binding on ELISA (as described in Section 2a) and also in an inhibition assay as described in Section 2c. A polyclonal antibody against HDL in goat obtained from MEDIX Corporation was also used.

Horseradish peroxidase (1 mg=155 Ku, Amano International) was dissolved in water (250 µL) and oxidized with freshly prepared 0.2 M sodium meta-periodate (50 µl) at room temperature in the dark for 20 minutes. The oxidized peroxidase was then dialyzed against 2 liters of 1 mM acetate buffer (pH 4.5) at 4° C. for four hours.

Monoclonal antibody against apoB (Mab 1 -1182-137, 1.9 mg/mL), which was dialyzed against 0.01 M carbonate buffer (pH 9.5) at 4° C., was treated with 20 µL of 0.2 M carbonate buffer (pH 9.5). The antibody and the dialyzed peroxidase were then mixed at room temperature in the dark for two hours. To this mixture 24 µL of freshly prepared sodium borohydride (Aldrich, 4 mg/mL in water) was added and then incubated at 4° C. in the dark for two hours. The peroxidase-antibody conjugate was then dialyzed against two liters of 20 mM phosphate buffered saline (pH 7.4) at 4° C. and stored at −20° C. in small aliquots.

Similar procedure was adopted to prepare the peroxidase conjugate of anti-HDL polyclonal antibody.

Figure 8A:
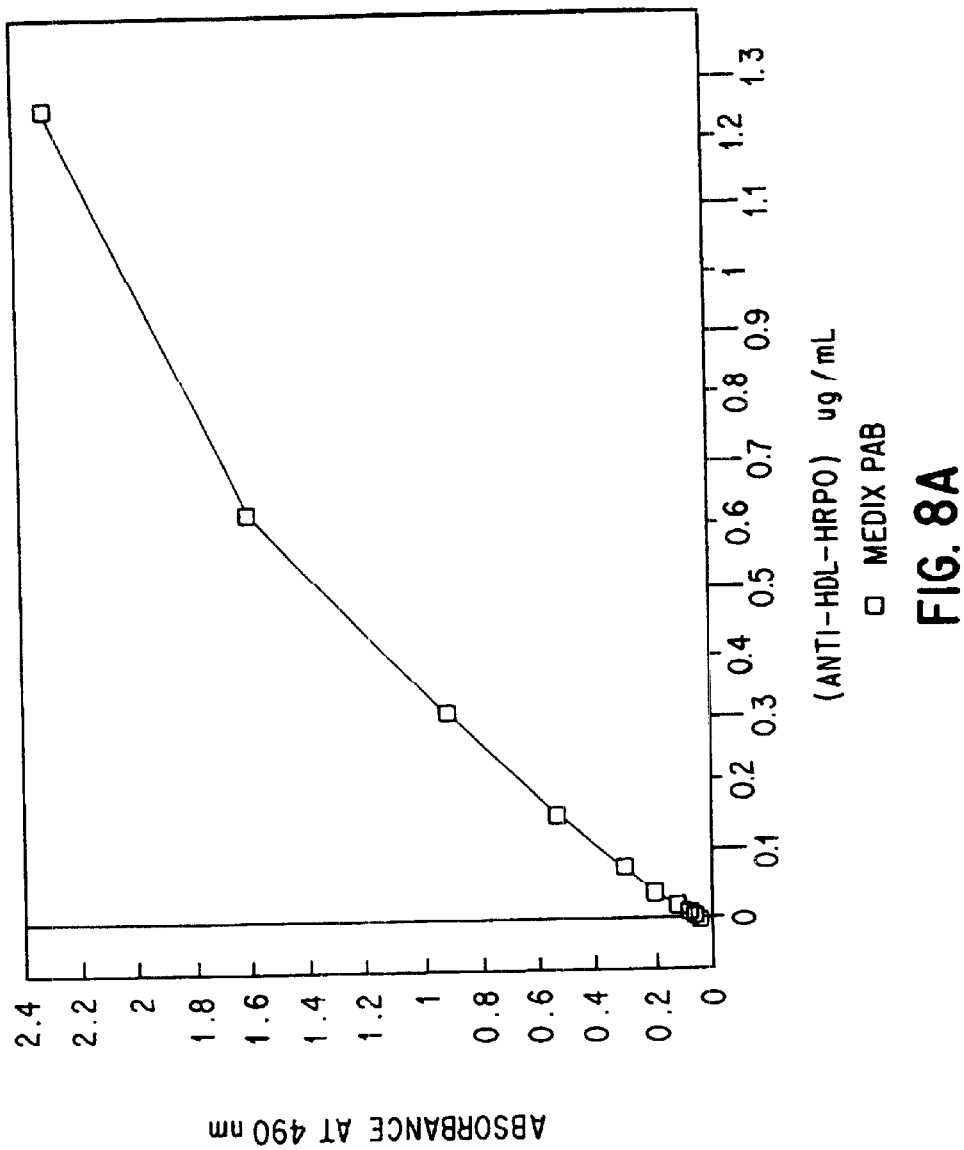
FIG. 8: A is typical binding curves of the HRPO-labelled anti-HDL polyclonal antibody with HDL. B is a typical binding curve of the HRPO-labelled anti-apoB monoclonal antibody with LDL, VLDL, IDL and HDL. Both are as described in Example 2.
Figure 8B:
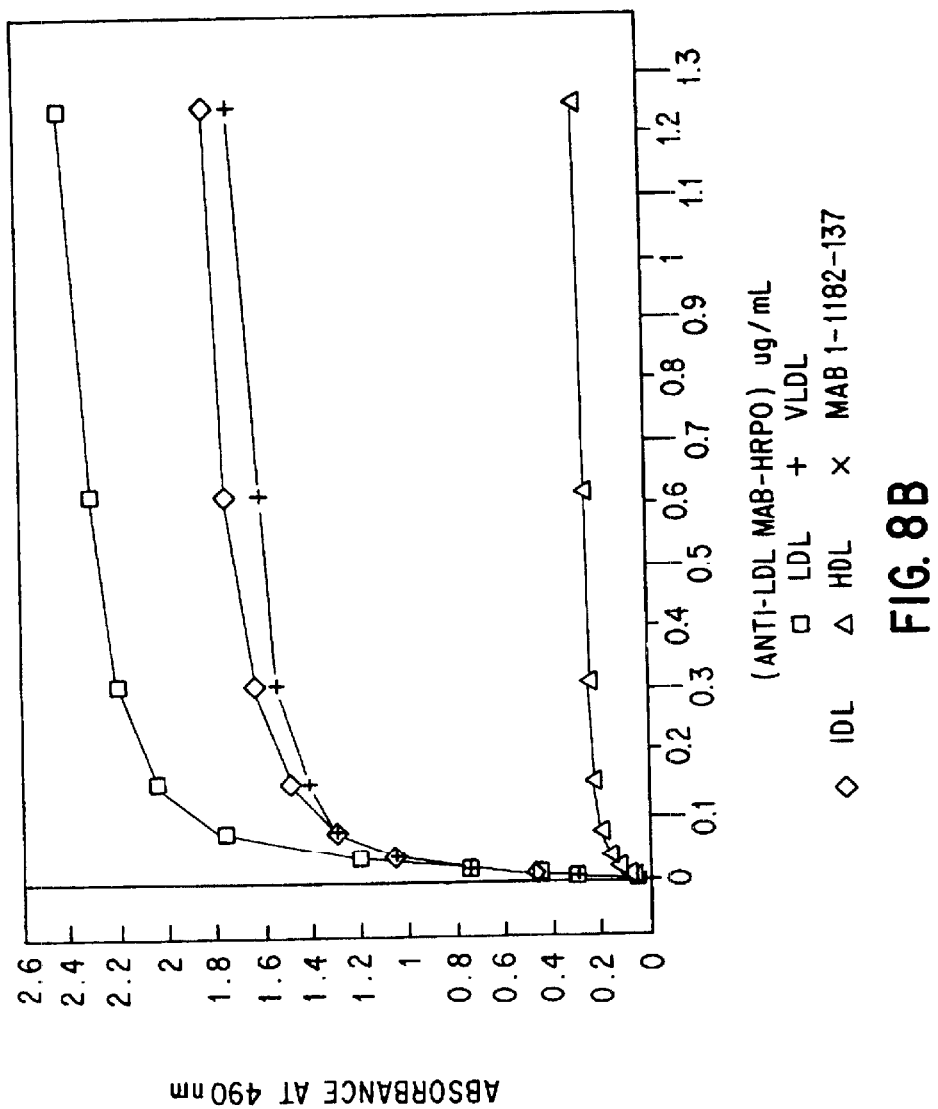

The binding curves of anti-apoB and anti-HDL-peroxidase conjugates with lipoproteins are shown in FIGS. 8A and 8B, respectively. A Maxisorb Nunc Immuno plate was coated with 100 µl of different lipoproteins by incubation at 37° C. for 30 minutes. After blocking the non-specific sites with 200 µl of 10% FBS in PBS at 37° C. for one hour, and washing five times with PBS-Tween 20, 100 µL of peroxidase conjugates (2.5 µg/mL diluted in 3% FBS in PBS) was added to the first row of wells and were serially diluted in horizontal wells. The plates were incubated at 37°

C. for 30 minutes, washed eight times with PBS-Tween 20. One hundred microliters of OPD substrate solution was added to each well. After incubation at room temperature for five minutes, the color reaction was stopped with 100 μl of 1 N $H_2SO_4$. The plate was then read at 490 nm on a microplate reader.

EXAMPLE 3
Covalent Attachment of Monoclonal Antibody to Cnbr-Activated Sepharose 4b One gram of CNBr-activated Sepharose 4B (Pharmacia LKB, Piscataway, N.J.) was suspended in about 15 mL of 1 mM HCI. The gel was then transferred to a coarse-porosity sintered-glass funnel and washed with 25 mL of 0.1 M carbonate buffer in 0.5 M sodium chloride, pH 8.3 (coupling buffer). A gentle vacuum was applied to remove the buffer. The moist gel cake was then transferred to a glass tube with a screw-capped stopper. Monoclonal antibody 18-258-211 (15 mg, concentration 2.6 mg/mL), which was dialyzed against the coupling buffer at 4° C., was then added to the gel. The mixture was then mixed gently end-over-end using an infiltration wheel at 4° C. for 20 hours. The supernatant was checked by measuring the absorbance at 280 nm for the unbound antibody. For all monoclonal antibodies used, more than 95% were bound to the gel. The gel was then transferred to a coarse-porosity sintered-glass funnel, washed with 50 mL of the coupling buffer and then with 25 mL of 0.1 M TRIS-HCI buffer, pH 8.0 (blocking buffer). The gel was then transferred to a glass tube, and mixed with 10 mL of the blocking buffer at room temperature for two hours. The antibody-immobilized gel was then washed with three cycles of alternating pH. Each cycle consisted of a wash with acetate buffer (0.1 M, pH 4) containing sodium chloride (0.5 M) followed by a wash with TRIS buffer (0.1 M, pH 8) containing sodium chloride (0.5 M). The final wash was done with 100 mL of TRIS-HCI buffer (0.05 M pH 7.4) containing sodium chloride (0.15 M) and sodium azide (0.01%) (storage buffer). The gel was stored as a 25% suspension (14 mL) in the storage buffer at 4° C. Assuming 100% of the monoclonal antibody bound to the gel, 200 μL of gel suspension contains 214 μg of the monoclonal antibody.

EXAMPLE 4
Preparation of Cholesterol Assay Reagents a. Reagents: Two separate reagents were prepared and were mixed together at the time of the assay. The first reagent formula was comprised of 1.62 g of 3,5dichloro-2-hydroxy-benzenesulfonic acid sodium salt (Aldrich, Milwaukee, Wis.) and 0.428 g of horseradish peroxidase (specific activity 82.3 EZ/mg, Amano International) dissolved in 20.4 mL 0.05 M of 3-(N-morpholino)-2-hydroxypropanesulfonic acid sodium salt (MOPSO, SIGMA) at pH 7. The second reagent formaia was comprised of 0.0113 g $MgCl_2$. $6H_2O$, 0.0276 g anhydrous $CaCl_2$, 0.51 g lactose, 0.51 g dextran (M.W. 17,900, Pharmachem, Terrytown, N.Y.), 1.02 g bovine serum albumin (fatty acid free, SIGMA), 0.30 g glycerol, 0.187 g 4-aminoantipyrine (ALDRICH, Milwaukee, Wis.)), 0.1486 g cholesterol ester hydrolase (specific activity 8.4 EZ/mg, Amano International), 0.086 g cholesterol oxidase (specific activity 6.2 EZ/mg, Boehringer-Mannheim) dissolved in 10.2 mL of 0.25 M MOPSO buffer (pH 7). The first and the second reagents were stored separately in small aliquots at −20° C. in dark.

Both reagents have been found to be stable for at least 16 months in terms of their assay performances, in terms of correlation and slope with known cholesterol standards. Eight and one half microliters of each of the reagents were used in the assay. The peroxidase activity of 8.5, μL of first reagent was 14.7 EZ and the enzyme activities of cholesterol ester hydrolase and cholesterol oxidase of the second reagent were 1.04 EZ and 0.445EZ, respectively.

b. Reaction Buffer: The reaction buffer (ICMT) which is also the extraction buffer contained the following materials: 0.05 M MOPSO (pH 7) (Sigma), 1% IgePal CO-530 (GAF), 0.2% Triton- X-100® (Bio-Rad) and 0.3% cholic acid (Sigma). The buffer was sterile filtered and was stored at room temperature. The buffer is stable for at least one year.

EXAMPLE 5
Preparation of a VLDL-Cholesterol Standard Curve

Two hundred microliters of monoclonal antibody-immobilized Sepharose 4B gel suspension from Example 3 was transferred to an appropriate number of Eppendorf microcentrifuge tubes. Each tube was completely filled with 5% BSA in PBS and mixed on a TOMY micro tube mixer (Peninsula Laboratories) at room temperature for one hour in order to block the non-specific binding sites of the plastic tube. Tubes were then centrifuged on a table-top centrifuge for about one minute and the supernatant carefully aspirated. One hundred microliters of a plasma sample diluted in PBS was added to a tube of gel suspension. Gel suspensions were mixed on a TOMY mixer at room temperature for one hour. Gel suspensions were then washed twice with about 1 mL of PBS by mixing for one minute, centrifuging for one minute and aspirating the supernatant from each. ICMT solution (prepared as in Example 4(b)) was added to each tube to a final volume of 750 μL. Cholesterol assay reagents (8.5 μL of each of #1 and #2 from Example 4 (a)) were added to each tube. The suspensions were mixed on a TOMY mixer for about eight minutes, centrifuged for one minute and the absorbances of the supernatant solutions were read on a DU 7400 Spectrophotometer at 515 nm. The concentrations of the gel-bound cholesterol were determined from a cholesterol standard curve. The standard curve (shown in FIG. 6) was prepared with purified VLDL samples having concentrations of 1.56, 3.12, 6.25, 12.5 and 25 mg/dL following the assay protocol described above.

EXAMPLE 6
VLDL-Cholesterol Immunocapture Assay

Two hundred microliters of monoclonal antibody-immobilized Sepharose 4B gel suspension from Example 3 (about 214 μg of antibody) was transferred to an appropriate number of Eppendorf tubes which were previously treated with 5% BSA in PBS to block all non-specific binding sites. One hundred microiters of individual plasma samples (containing acid-citrate-dextrose or EDTA anticoagulant), diluted ten-fold in PBS, were added to each 200 μL of gel suspension. The gel suspensions were mixed on a TOMY mixer at room temperature for one and a half hours. The gel suspensions were then washed with about 1 mL of PBS by mixing for one minute, centrifuging for one minute and aspirating the supernatants. ICMT solutions (described in Example 4(b)) were added to each tube to a final volume of 750 μL. Cholesterol assay reagent (8.5 μl of each of #1 and #2 from Example 4(a)) were added to each tube. The suspensions were mixed on a TOMY mixer for about eight minutes, centrifuged for one minute and the absorbances of the supetnatant solutions were read on a DU 7400 Spectrophotometer at 515 nm. The concentrations of VLDL-cholesterol in the plasma samples were determined by multiplying the concentration obtained from the standard curve shown in FIG. 6 by 10. The results are shown in Table 6 and FIG. 7.

EXAMPLE 7
Quantitation of VLDL-Cholesterol by Ultracentrifugation

Plasma samples (2 mL each) were transferred to ultraclear tubes (Beckman, 11×34 mm) and then overlayered with 0.3 mL of d 1.006 g/mL KBr solution. The samples were centrifuged on a TLS 55 swinging bucket rotor at 40,000 rpm at 4° C. for 20 hours using a T-100 Beckman ultracentrifuge. The upper VLDL layers were carefully pipetted out without disturbing the bottom layer. Phosphate buffered saline, pH 7.4 was added to the centrifuged tube to bring the volume to the original mark (2.3 mL). Adequate recovery was verified by comparing the sum of cholesterol in each of the fractions to the total cholesterol of the sample. The cholesterol concentrations of the upper VLDL and the lower d>1.006 g/mL (infranet cholesterol) were determined with VISION cholesterol assays (Abbott Laboratories, Abbott Park, Ill.). VLDL-cholesterol concentrations were calculated as the difference between total plasma cholesterol and infranet cholesterol. The results are shown in Table 5 and were used in the correlation studies in Table 6.

EXAMPLE 8
VLDL-Cholesterol Sandwich Assay

The monoclonal antibody 18-358-211 was diluted in 20 mM PBS, at pH 7.4, to a concentration of 15 µg/mL. One hundred microliters of the antibody solution was added to the wells of Maxisorb Nunc Immuno plates and the plates were incubated at room temperature on a rotator at 100 rpm for two hours. The plates were washed five times with PBS-Tween solutions and then blocked with 200 µl of 5% w/v BSA in 20 mM PBS, at pH 7.4, by incubation at 37° C. for one hour. The plates can be stored at 4° C. with plastic sealers at least for ten days prior to use.

Plasma samples (Nos. 1–75 in Table 5) were diluted 125-fold with 1 % w/v alkali-treated casein in 20 mM PBS at pH 7.4. One hundred microliters of the diluted samples were added to each well of the antibody plates and the plates were incubated at 37° C. for one hour. After washing the plates five times with PBS-Tween, 100 µl of HRPO-digitonin conjugate (0.5 µg/mL in 1% w/v alkali-treated casein in 20 mM PBS at pH 7.4) were added to each well. The plates were incubated at 37° C. for one hour and then washed ten times with PBS-Tween. One-hundred microliters of a freshly prepared solution of o-phenylenediamine in citrate buffer (substrate commercially available from Abbott Laboratories) were added to each well and after five minutes, the reaction was quenched with 100 µL of 1 N $H_2SO_4$. The absorbance of each well was measured on a Bio-Tek microplate reader at 490 nm. The VLDL-cholesterol concentration was then determined from a standard curve of absorbance versus VLDL-cholesterol concentration (shown in FIG. 9). The results of the sandwich assay and the correlation curve between the ultracentrifuge method and sandwich assay for VLDL-cholesterol are shown in Table 6 and FIG. 10. The correlation between the two methods were fairly good with a correlation coefficient (r)=0.923; intercept=−0.251 and slope=1.00. The correlation between the two methods could have been even better if the VLDL-cholesterol concentrations could have been more direct Moreover, calculation by using two assays (total cholesterol and infranet cholesterol in the ultra centrifuged fraction) obviously can lead to an error, particularly with plasma samples with low VLDL cholesterol concentrations.

EXAMPLE 9
VLDL-Cholesterol Calibration Curve for Immunocapture Assay

VLDL-cholesterol standards were prepared from plasma samples as described in Section 6. Calibrators having VLDL-cholesterol concentrations of 0, 1.56, 3.125, 6.25, 12.5 and 25 mg/dL were assayed by the method described in Example 9. The concentrations were multiplied by 125 to generate the standard curve because the plasma samples were diluted 125-fold prior to performing the assay. A plot of VLDL-cholesterol concentration versus absorbance was prepared from the resulting data. FIG. 8 is illustrative of such a plot The VLDL-cholesterol concentration in unknown samples can be determined from the calibration curve. Generally the calibrators and the plasma samples were assayed on the same plate to minimize the effect of variations in the reagents, materials and conditions. The number and concentration of calibrators can be readily altered depending on the desired accuracy of the results.

The embodiments described and the alternative embodiments presented are intended as examples rather than as limitations. Thus, the description of the invention is not intended to limit the invention to the particular embodiments disclosed, but it is intended to encompass all equivalents and subject matter within the spirit and scope of the invention as described above and as set forth in the following claims.

TABLE 5
LIPID PROFILES OF PLASMA SAMPLES

| Sample No. | Total-C mg/dL | HDL-C mg/dL | Trig[1] mg/dL | FE-LDL[2] mg/mL | FE-LDL[3] mg/mL |
|---|---|---|---|---|---|
| 1 | 155 | 68 | 107 | 107 | 107 |
| 2 | 220 | 44 | 201 | 136 | 144 |
| 3 | 197 | 55 | 44 | 133 | 128 |
| 4* | 230 | 47 | 109 | 150 | 166 |
| 5 | 177 | 38 | 104 | 118 | 119 |
| 6 | 182 | 70 | 37 | 104 | 104 |
| 7 | 217 | 41 | 127 | 150 | 156 |
| 8 | 135 | 43 | 77 | 77 | 78 |
| 9* | 227 | 32 | 365 | 122 | 137 |
| 10 | 282 | 43 | 180 | 203 | 196 |
| 11 | 275 | 50 | 114 | 202 | 174 |
| 12 | 199 | 65 | 249 | 84 | 102 |
| 13 | 231 | 50 | 73 | 166 | 163 |
| 14 | 179 | 49 | 64 | 117 | 117 |
| 15 | 136 | 35 | 92 | 83 | 85 |
| 16 | 228 | 59 | 110 | 147 | 138 |
| 17 | 142 | 51 | 51 | 81 | 81 |
| 18 | 170 | 64 | 45 | 97 | 97 |
| 19 | 205 | 65 | 126 | 115 | 125 |
| 20 | 127 | 45 | 58 | 71 | 75 |
| 21 | 172 | 64 | 70 | 94 | 99 |
| 22 | 207 | 67 | 50 | 130 | 134 |
| 23 | 211 | 40 | 99 | 150 | 147 |
| 24 | 178 | 56 | 70 | 87 | 90 |
| 25 | 156 | 63 | 51 | 83 | 75 |
| 26 | 225 | 45 | 93 | 161 | 158 |
| 27 | n/a | r/a | n/a | n/a | n/a |
| 28 | 166 | 51 | 64 | 102 | 104 |
| 29 | 142 | 51 | 44 | 82 | 82 |
| 30 | 162 | 67 | 162 | 62 | 67 |
| 31 | 161 | 70 | 94 | 72 | 70 |
| 32 | 187 | 45 | 215 | 99 | 106 |
| 33 | 147 | 49 | 67 | 85 | 81 |
| 34 | 144 | 38 | 78 | 90 | 87 |
| 35 | 185 | 78 | 36 | 100 | 101 |
| 36 | 177 | 39 | 133 | 111 | 115 |
| 37 | 148 | 29 | 168 | 86 | 89 |
| 38 | 182 | 58 | 84 | 108 | 93 |
| 39 | 203 | 36 | 57 | 156 | 150 |
| 40 | 119 | 45 | 64 | 62 | 64 |
| 41 | 138 | 48 | 90 | 71 | 76 |
| 42 | 156 | 26 | 125 | 105 | 109 |
| 43 | 190 | 46 | 102 | 123 | 108 |
| 44 | 258 | 36 | 368 | 149 | 148 |
| 45* | 209 | 41 | 146 | 139 | 124 |
| 46 | 160 | 60 | 41 | 92 | 97 |
| 47 | 181 | 47 | 60 | 123 | 123 |

TABLE 5-continued

LIPID PROFILES OF PLASMA SAMPLES

| Sample No. | Total-C mg/dL | HDL-C mg/dL | Trig[1] mg/dL | FE-LDL[2] mg/mL | FE-LDL[3] mg/mL |
|---|---|---|---|---|---|
| 48 | 222 | 38 | 106 | 162 | 158 |
| 49 | 246 | 57 | 146 | 159 | 161 |
| 50 | 184 | 48 | 88 | 119 | 119 |
| 51 | 280 | 45 | 209 | 193 | 180 |
| 52 | 229 | 53 | 115 | 153 | 148 |
| 53 | 164 | 45 | 124 | 94 | 95 |
| 54 | 208 | 42 | 161 | 134 | 135 |
| 55 | 245 | 50 | 91 | 177 | 162 |
| 56 | 185 | 54 | 54 | 120 | 124 |
| 57 | 180 | 66 | 62 | 102 | 99 |
| 58* | 164 | 42 | 85 | 105 | 105 |
| 59* | 244 | 55 | 132 | 163 | 140 |
| 60 | 167 | 33 | 154 | 103 | 120 |
| 61 | 175 | 53 | 102 | 102 | 104 |
| 62 | 151 | 55 | 169 | 62 | 75 |
| 63 | 180 | 36 | 205 | 103 | 107 |
| 64 | 230 | 54 | 122 | 151 | 142 |
| 65 | 181 | 42 | 92 | 121 | 116 |
| 66 | 184 | 50 | 132 | 108 | 110 |
| 67 | 206 | 37 | 247 | 120 | 129 |
| 68 | 139 | 46 | 59 | 71 | 75 |
| 69 | 167 | 46 | 73 | 106 | 105 |
| 70 | 215 | 63 | 78 | 136 | 134 |
| 71 | 148 | 71 | 53 | 67 | 73 |
| 72 | 156 | 42 | 64 | 102 | 91 |
| 73 | 162 | 53 | 95 | 90 | 95 |
| 74 | 216 | 34 | 142 | 154 | 152 |
| 75 | 154 | 50 | 69 | 90 | 86 |
| 76 | n/a | n/a | n/a | n/a | n/a |
| 77 | 136 | 38 | 65 | 85 | 72 |
| 78 | 160 | 49 | 61 | 99 | 89 |
| 79 | 165 | 72 | 98 | 73 | 75 |
| 80 | 147 | 46 | 62 | 89 | 77 |
| 81 | 160 | 49 | 86 | 94 | 72 |
| 82 | 173 | 29 | 98 | 124 | 113 |
| 83 | 161 | 38 | 96 | 104 | 82 |
| 84 | 176 | 90 | 45 | 77 | 83 |
| 85 | 161 | 48 | 84 | 96 | 95 |
| 86 | n/a | n/a | n/a | n/a | n/a |
| 87 | 198 | 80 | 54 | 107 | 110 |
| 88 | 207 | 75 | 79 | 115 | 120 |
| 89 | 115 | 46 | 67 | 56 | 58 |
| 90 | n/a | n/a | n/a | n/a | n/a |
| 91 | n/a | n/a | n/a | n/a | n/a |
| 92 | 180 | 55 | 49 | 115 | 110 |
| 93* | 238 | 40 | 214 | 155 | 163 |
| 94* | 289 | 36 | 299 | 193 | 202 |
| 95* | 228 | 70 | 91 | 140 | 144 |
| 96* | 309 | 39 | 68 | 256 | 266 |
| 97** | 200 | 34 | 341 | 98 | 129 |
| 98** | 135 | 38 | 53 | 86 | 89 |
| 99** | 237 | 53 | 316 | 121 | 138 |
| 100** | 200 | 41 | 234 | 112 | 106 |

[1]Trig = triglyceride concentration
[2]FE = Friedewald Equation: [LDL – Chol] = [Total – Chol] – [HDL – Chol] – [Trig/5]
[3]UC = Ultracentrifuge β-quantitation: [LDL – Chol] = [d.1.006 g/mL Infranate – Chol] – [HDL – Chol]
*Patients with coronary heart disease who are on lipid lowering drugs
**Diabetic patients

TABLE 6

CORRELATION BETWEEN VLDL-CHOLESTEROL ASSAYS

| Sample No. | UC-VLDL[1] mg/dL | IC-VLDL[2] mg/dL | IA-VLDL[3] mg/dL |
|---|---|---|---|
| 1 | 14 | 9 | 11 |
| 2 | 20 | 17 | 20 |
| 3 | 14 | 12 | 9 |
| 4 | 17 | 13 | 20 |
| 5 | 17 | 15 | 18 |
| 6 | 8 | 10 | 10 |
| 7 | 20 | 17 | 18 |
| 8 | 14 | 11 | 12 |
| 9 | 60 | 68 | 73 |
| 10 | 46 | 55 | 51 |
| 11 | 51 | 49 | 56 |
| 12 | 32 | 21 | 21 |
| 13 | 14 | 10 | 14 |
| 14 | 13 | 12 | 12 |
| 15 | 12 | 10 | 9 |
| 16 | 22 | 21 | 22 |
| 17 | 10 | 8 | 8 |
| 18 | 9 | 8 | 5 |
| 19 | 15 | 12 | 18 |
| 20 | 7 | 12 | 8 |
| 21 | 14 | 14 | 21 |
| 22 | 10 | 11 | 11 |
| 23 | 15 | 12 | 15 |
| 24 | 14 | 13 | 9 |
| 25 | 10 | 8 | 6 |
| 26 | 14 | 11 | 14 |
| 27 | 8 | 6 | 4 |
| 28 | 11 | 10 | 9 |
| 29 | 12 | 15 | 12 |
| 30 | 28 | 29 | 30 |
| 31 | 26 | 20 | 22 |
| 32 | 37 | 35 | 44 |
| 33 | 18 | 13 | 12.4 |
| 34 | 21 | 18 | 12.4 |
| 35 | 11 | 16 | 12 |
| 36 | 23.5 | 23.9 | 28 |
| 37 | 31 | 23 | 30 |
| 38 | 33 | 25 | 24 |
| 39 | 19 | 19 | 17 |
| 40 | 14 | 12.4 | 14 |
| 41 | 16 | 17 | 18 |
| 42 | 22 | 21.5 | 18 |
| 43 | 40 | 21 | 36 |
| 44 | 77 | 80 | 76 |
| 45 | 42 | 31 | 31 |
| 46 | 10 | 13 | 15 |
| 47 | 16 | 14.4 | 18 |
| 48 | 21 | 20 | 17 |
| 49 | 29 | 33 | 27.4 |
| 50 | 20.5 | 20.7 | 20 |
| 51 | 57 | 61 | 49 |
| 52 | 31 | 28 | 28 |
| 53 | 27 | 23 | 29 |
| 54 | 18 | 28 | 30 |
| 55 | 30 | 20 | 19 |
| 56 | 13 | 16.8 | 21 |
| 57 | 16 | 15.6 | 16.8 |
| 58 | 18 | 16 | 18 |
| 59 | 40 | 41 | 34 |
| 60 | 18 | 23 | 23.7 |
| 61 | 20 | 19.2 | 19.5 |
| 62 | 27 | 32.8 | 47 |
| 63 | 39 | 49 | 49 |
| 64 | 39 | 44 | 31 |
| 65 | 22.5 | 24.5 | 22 |
| 66 | 31 | 31.6 | 30 |
| 67 | 41 | 50 | 49 |
| 68 | 13 | 13 | 14 |
| 69 | 21 | 19.3 | 18 |
| 70 | 24 | 23 | 17 |
| 71 | 10 | 14 | 10 |
| 72 | 15 | 19 | 14 |
| 73 | 19 | 18 | 21 |
| 74 | 33 | 33.7 | 31.2 |
| 75 | 22 | 28 | 32 |
| 76 | 10 | 9 | |
| 77 | 13 | 10 | |
| 78 | 12 | 14 | |

TABLE 6-continued

CORRELATION BETWEEN VLDL-CHOLESTEROL ASSAYS

| Sample No. | UC-VLDL[1] mg/dL | IC-VLDL[2] mg/dL | IA-VLDL[3] mg/dL |
|---|---|---|---|
| 79 | 14 | 10 | |
| 80 | 12 | 10 | |
| 81 | 16 | 11 | |
| 82 | 20 | 18 | |
| 83 | 19 | 19 | |
| 84 | 9 | 13 | |
| 85 | 10 | 8 | |
| 86 | 7 | 12 | |
| 87 | 12 | 15 | |
| 88 | 14 | 18 | |
| 89 | 11 | 9 | |
| 90 | 15 | 9 | |
| 91 | 8 | 4 | |
| 92 | 15 | 14 | |
| 93 | 37 | 43 | |
| 94 | 51 | 50 | |
| 95 | 11 | 11 | |
| 96 | 14 | 17 | |
| 97 | 37 | 37 | |
| 98 | 8 | 5 | |
| 99 | 35 | 31 | |
| 100 | 52 | 53 | |

[1]Measured by Ultracentrifugation according to Example 7.
[2]Measured by immunocapture according to Example 6.
[3]Measured by sandwich immunoassay according to Example 8.

What is claimed is:

1. A method for determining the amount of apoB associated with very low density lipoprotein (VLDL) in a sample comprising the steps of:
   (a) mixing a sample and a VLDL-specific binding agent for a time and under conditions to form binding-agent-VLDL complexes, wherein said VLDL-specific binding agent is an antibody or fragment thereof that binds to substantially all VLDL, to low density lipoprotein (LDL) at less than about 10% of VLDL binding, to intermediate density lipoprotein (IDL) at less than about 10% of VLDL binding, and to high density lipoprotein (HDL) at less than about 10% of VLDL binding; and
   (b) determining the amount of apoB associated with VLDL bound to said binding-agent-VLDL complexes.

2. The method of claim 1 wherein said VLDL-specific binding agent is coupled to a solid support.

3. The method of claim 2 further comprising the step of separating the solid support from the sample before determining the amount of apoB bound to said binding-agent-VLDL complexes.

4. The method of claim 2 wherein the solid support is selected from the group consisting of nitrocellulose, latex, nylon, and polystyrene.

5. The method of claim 2 wherein the solid support is selected from the group consisting of beads, particles, magnetic particles, and glass fiber.

6. The method of claim 1 further comprising the step of separating said binding-agent-VLDL complexes prior to step (b).

7. The method of claim 6 wherein said VLDL-specific binding agent is conjugated to a first charged substance and said separation comprises:
   (a) contacting said binding-agent-VLDL complexes with an insoluble solid phase material which is oppositely charged with respect to said first charged substance, such that said solid phase material attracts and attaches to said first charged substance; and
   (b) separating said solid phase material and said sample.

8. The method of claim 7 wherein said charged substances are anionic and cationic monomers or polymers.

9. The method of claim 1 wherein said antibody is a monoclonal antibody.

10. The method of claim 9 wherein said monoclonal antibody is produced by the hybridoma deposited as ATCC accession number HB-12392.

11. A method for determining the amount of apoB associated with very low density lipoprotein (VLDL) in a sample comprising the steps of:
   (a) contacting said sample with an indicator reagent wherein said indicator reagent is a monoclonal antibody or fragment thereof that binds to substantially all apoB associated with VLDL, to apoB associated with low density lipoprotein (LDL) at less than about 10% of VLDL binding, to apoB associated with intermediate density lipoprotein (IDL) at less than about 10% of VLDL binding, and to apoB associated with high density lipoprotein (HDL) at less than about 10% of VLDL binding and with a solid support coated with VLDL for a time and under conditions to permit binding of said indicator reagent with said VLDL in said sample and with said bound VLDL; and
   (b) determining said amount of apoB associated with VLDL in said test sample by detecting the reduction in binding of said indicator reagent to said solid support as compared to the signal generated from a negative sample to indicate the presence of VLDL in said test sample.

12. The method of claim 11 wherein said indicator reagent is produced by the hybridoma deposited as ATCC accession number HB-12392.

* * * * *